(12) United States Patent
Kume et al.

(10) Patent No.: US 9,617,517 B2
(45) Date of Patent: Apr. 11, 2017

(54) SMALL CHEMICAL COMPOUND WHICH PROMOTES INDUCTION OF DIFFERENTIATION OF STEM CELLS INTO INSULIN-PRODUCING CELLS AND METHOD FOR INDUCING DIFFERENTIATION OF STEM CELLS INTO INSULIN-PRODUCING CELLS USING SAID SMALL CHEMICAL COMPOUND

(75) Inventors: Shoen Kume, Kumamoto (JP); Daisuke Sakano, Kumamoto (JP); Nobuaki Shiraki, Kumamoto (JP); Kahoko Umeda, Kumamoto (JP); Taiji Yamazoe, Kumamoto (JP); Kazuhiko Kume, Kumamoto (JP); Motonari Uesugi, Kyoto (JP)

(73) Assignees: NATIONAL UNIVERSITY CORPORATION KUMAMOTO UNIVERSITY, Kumamoto (JP); KYOTO UNIVERSITY, Kyoto (JP)

( * ) Notice: Subject to any disclaimer, the term of this patent is extended or adjusted under 35 U.S.C. 154(b) by 230 days.

(21) Appl. No.: 14/115,618

(22) PCT Filed: May 1, 2012

(86) PCT No.: PCT/JP2012/061549
§ 371 (c)(1),
(2), (4) Date: Apr. 28, 2014

(87) PCT Pub. No.: WO2012/150707
PCT Pub. Date: Nov. 8, 2012

(65) Prior Publication Data
US 2014/0256043 A1    Sep. 11, 2014

(30) Foreign Application Priority Data

May 2, 2011    (JP) ............... 2011-103281

(51) Int. Cl.
| | | |
|---|---|---|
| *C12N 5/071* | (2010.01) |
| *A61K 45/06* | (2006.01) |
| *A61K 31/198* | (2006.01) |
| *A61K 31/221* | (2006.01) |
| *A61K 31/405* | (2006.01) |
| *A61K 31/407* | (2006.01) |
| *A61K 31/4375* | (2006.01) |
| *A61K 31/4745* | (2006.01) |
| *A61K 31/48* | (2006.01) |
| *A61K 31/525* | (2006.01) |
| *A61K 31/475* | (2006.01) |

(52) U.S. Cl.
CPC ......... *C12N 5/0676* (2013.01); *A61K 31/198* (2013.01); *A61K 31/221* (2013.01); *A61K 31/405* (2013.01); *A61K 31/407* (2013.01); *A61K 31/4375* (2013.01); *A61K 31/475* (2013.01); *A61K 31/4745* (2013.01); *A61K 31/48* (2013.01); *A61K 31/525* (2013.01); *A61K 45/06* (2013.01); *C12N 5/0678* (2013.01); *C12N 2501/115* (2013.01); *C12N 2501/385* (2013.01); *C12N 2506/02* (2013.01); *C12N 2510/00* (2013.01)

(58) Field of Classification Search
CPC ............ A61K 2300/00; Y10S 514/866; C12N 5/0623; G01N 33/5073
See application file for complete search history.

(56) References Cited

U.S. PATENT DOCUMENTS

| | | | |
|---|---|---|---|
| 4,322,398 | A | 3/1982 | Reiner et al. |
| 5,696,128 | A | 12/1997 | Cincotta et al. |
| 7,396,809 | B1 | 7/2008 | Lu et al. |
| 7,892,728 | B2 | 2/2011 | Moriyama et al. |

(Continued)

FOREIGN PATENT DOCUMENTS

| | | |
|---|---|---|
| EP | 1044976 A1 | 10/2000 |
| JP | 54-163807 A | 12/1979 |

(Continued)

OTHER PUBLICATIONS

Yi et al. The influence of histamine at various concentrations on the cell cycle state of hematopoietic stem cells (CFU-s). International Journal of Cell Cloning. 1988;6:290-295.*
Zahir et al. Neural stem/progenitor cells differentiate in vitro to neurons by the combined action of dibutyryl cAMP and interferon-gamma. Stem Cells and Development. 2009;18(10):1423-1432.*
D'Amour, K. A. et al. "Production of pancreatic hormone-expressing endocrine cells from human embryonic stem cells" Nat Biotechnol vol. 24, No. 11, pp. 1392-1401 (2006).
Kroon, E. et al. "Pancreatic endoderm derived from human embryonic stem cells generates glucose-responsive insulin-secreting cells in vivo" Nat Biotech vol. 26, 443-52 (2008).

(Continued)

*Primary Examiner* — Lynn Fan
(74) *Attorney, Agent, or Firm* — Michael Ye; Andrews Kurth Kenyon LLP

(57) ABSTRACT

A purpose of the present invention is to provide a small chemical compound which especially promotes induction of the differentiation of ES cells into insulin-producing cells. Another purpose of the present invention is to provide: a method for inducing the differentiation of ES cells into insulin-producing cells using the compound; and an agent for promoting induction of the differentiation into insulin-producing cells. Another purpose of the present invention is to provide the thus-induced insulin-producing cells. Provided are: an agent for promoting induction of the differentiation of stem cells derived from a mammal into insulin-producing cells, which contains a compound that is selected from the group consisting of dopamine metabolism inhibitors, serotonin metabolism inhibitors, acetylchotine, acetylcholine degrading enzyme inhibitors and acetylcholine receptor activators; and a method for inducing differentiation using the agent for promoting induction of differentiation.

11 Claims, 12 Drawing Sheets

(56) References Cited

U.S. PATENT DOCUMENTS

| | | | |
|---|---|---|---|
| 7,951,797 | B2 | 5/2011 | Breslin et al. |
| 8,158,635 | B2 | 4/2012 | Beauchamps et al. |
| 8,247,229 | B2 | 8/2012 | Odorico et al. |
| 8,278,453 | B2 | 10/2012 | Kuduk et al. |
| 8,309,353 | B2 | 11/2012 | Kume et al. |
| 8,399,408 | B2 | 3/2013 | Austen et al. |
| 8,470,873 | B2 | 6/2013 | Chen |
| 2010/0021437 | A1* | 1/2010 | Isacson ............ C12N 5/0618 424/93.7 |
| 2010/0137202 | A1 | 6/2010 | Yang |
| 2011/0003741 | A1 | 1/2011 | Austen et al. |

FOREIGN PATENT DOCUMENTS

| | | | |
|---|---|---|---|
| JP | 5-504548 | | 7/1993 |
| JP | 2008-11848 | A | 12/1997 |
| JP | 2009-46504 | A | 3/2009 |
| JP | 2009-525342 | A | 7/2009 |
| JP | 2010-507673 | A | 3/2010 |
| JP | 2011-128 | A | 1/2011 |
| JP | 2011-010653 | A | 1/2011 |
| JP | 2011-68679 | A | 4/2011 |
| WO | 91/04037 | A1 | 4/1991 |
| WO | 99/32125 | A1 | 7/1999 |
| WO | WO02086107 | * | 10/2002 ............ C12N 5/08 |
| WO | WO 2006/126574 | A1 | 11/2006 |
| WO | WO2007008758 | * | 1/2007 ............ G01N 33/50 |
| WO | WO 2007/058105 | A1 | 5/2007 |
| WO | 2010/051223 | A1 | 5/2010 |
| WO | 2010/070618 | A2 | 6/2010 |
| WO | 2010/132605 | A1 | 11/2010 |
| WO | WO 2010/140464 | A1 | 12/2010 |
| WO | 2011/011300 | A2 | 1/2011 |
| WO | 2011/030915 | A1 | 3/2011 |

OTHER PUBLICATIONS

Tateishi, K. et al. "Generation of insulin-secreting islet-like clusters from human skin fibroblasts" J Biol Chem vol. 283, pp. 31601-31607 (2008).

Shiraki N, et al. "Differentiation of mouse and human embryonic stem cells into hepatic lineages" Genes Cells., vol. 13, pp. 731-746 (2008).

Shiraki N, et al. "Guided differentiation of embryonic stem cells into Pdx1-expressing regional-specific definitive endoderm" Stem Cells. vol. 26, pp. 874-885 (2008).

Shiraki N, et al. "Differentiation and characterization of embryonic stem cells into three germ layers" Biochem Biophys Res Commun. vol. 381 pp. 694-699 (2009).

Kim, P. T. W. et al. "Differentiation of mouse embryonic stem cells into endoderm without embryoid body formation" Plos one, vol. 5, No. 11, pp. 1-8 (2010).

Lein, L. et al. "Inhibition of Abcg2 transporter on primitive hematopoietic stem . . . " vol. 30, No. 1, pp. 55-62 (2010).

Translation of written opinion of PCT/JP2012/064549.

Deval C et al: "Amino-acid limitation induces the GCN2 signaling pathway in myoblasts . . . myotubes", Biochimie, Masson, Paris, FR, vol. 90, No. 11-12, Nov. 1, 2008 pp. 1716-1721.

P Pohjanpelto et al: "Deprivation of a single amino acid inducesmRNAs in Chinese hamster . . . ovary cells. c-jun, c-myc and . . . cells" Mol. Cell. Biol, Jan. 1, 1990, pp. 5814-5821.

Alain Bruhat et al: "Amino acid limitation regulates gene expression", Proceedings of the Nutrition Society, vol. 58, No. 03, Aug. 1, 1999, pp. 625-632.

Jousse C et al: "Amino acid limitation regulates CHOP expression . . . unfolded protein response", FEBS Letters, Elsevier, Amsterdam, NL, vol. 448, No. 2-3, Apr. 9, 1999 pp. 211-216.

H N Jones et al: "Expression and adaptive regulation of amino acid . . . A in a placental cell line under amino acid restriction",Reproduction, vol. 131, No. 5, May 1, 2006 pp. 951-960.

J. Wang et al: "Metabolic Specialization of Mouse Embryonic Stem Cells", Cold Spring Harbor Symposia on Quantitative Biology, vol. 76, No. 0, Jan. 1, 2011, pp. 183-193.

N. Fontanier-Razzaq et al: "Nutrient-Gene Interactions Amino Acid Deficiency Up-regulates Specific mRNAs in Murine Embryonic Cells 1", J. Nutr., Jan. 1, 2002, pp. 2137-2142.

Wang Z et al: "Amino acid limitation induces down-regulation of WNT5a . . . level", Biochem. & Biophy. Res. Comm, Academic Press Inc., vol. 378, No. 4, Jan. 23, 2009 pp. 789-794.

J. M. Ryu et al: "L-Threonine Regulates G1/S Phase Transition of Mouse Embryonic Stem Cells . . . , and mTORC Pathways",J. of Bio.Chem., vol. 286, No. 27, May 6, 2011, pp. 23667-23678.

Nobuaki Shiraki et al: "Guiding ES cell differentiation into the definitive endoderm lineages", Inflammation and Regeneration, vol. 30, No. 2, Mar. 1, 2010, pp. 109-114.

J. Wang et al: "Dependence of Mouse Embryonic Stem Cells on Threonine Catabolism", Science, vol. 325, No. 5939, Jul. 9, 2009 (Jul. 9, 2009), pp. 435-439.

Shan Jixiu et al: "Activation of the amino acid response . . . stem cells", Am J. of Physio.: Endo & Metabolism, AM. Physio. Soc, Bethesda, MD, US,vol. 305 No. 3, Aug. 1, 2013 pp. E325-E335.

European Search Report from European Application No. 11836133.6 dated Apr. 30, 2014.

* cited by examiner

SEQUENCE LISTING

```
<160> NUMBER OF SEQ ID NOS: 32

<210> SEQ ID NO 1
<211> LENGTH: 18
<212> TYPE: DNA
<213> ORGANISM: Artificial Sequence
<220> FEATURE:
<223> OTHER INFORMATION: Synthetic DNA

<400> SEQUENCE: 1
tcgtattcca acaggagg                                                   18

<210> SEQ ID NO 2
<211> LENGTH: 18
<212> TYPE: DNA
<213> ORGANISM: Artificial Sequence
<220> FEATURE:
<223> OTHER INFORMATION: Synthetic DNA

<400> SEQUENCE: 2
aggcttttgc ttcaccag                                                   18

<210> SEQ ID NO 3
<211> LENGTH: 24
<212> TYPE: DNA
<213> ORGANISM: Artificial Sequence
<220> FEATURE:
<223> OTHER INFORMATION: Synthetic DNA

<400> SEQUENCE: 3
cttaaaccga tgggcgatct cact                                            24

<210> SEQ ID NO 4
<211> LENGTH: 22
<212> TYPE: DNA
<213> ORGANISM: Artificial Sequence
<220> FEATURE:
<223> OTHER INFORMATION: Synthetic DNA

<400> SEQUENCE: 4
ccccactagc ctctggcaaa at                                              22

<210> SEQ ID NO 5
```

```
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
caggcaatcc tgcaggaaca a                                                    21

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
cacttgcgga taactgtgcc a                                                    21

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
gtgatggtgg gaatgggtca                                                      20

<210> SEQ ID NO 8
<211> LENGTH: 22
<212> TYPE: DNA
<213> ORGANISM: Artificial Sequence
<220> FEATURE:
<223> OTHER INFORMATION: Synthetic DNA

<400> SEQUENCE: 8
tttgatgtca cgcacgattt cc                                                   22

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
gtcctacaga ttgacaatgc                                                      20

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
cacgctctgg atctgtgaca g                                                    21

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
```
actcacaggg cacattcacc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
ccagttgatg aagtccctgg                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
cagcccttag tgaccagcta                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
atgctggtgc agcactgatc                                               20

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15
ccaaaaccgt cgcatgaagt g                                             21

<210> SEQ ID NO 16
<211> LENGTH: 23
<212> TYPE: DNA
<213> ORGANISM: Artificial Sequence
<220> FEATURE:
<223> OTHER INFORMATION: Synthetic DNA

<400> SEQUENCE: 16
ctctcgtgcc ctcaagaatt ttc                                           23

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
aggatggccg tcgcatactg                                               20

<210> SEQ ID NO 18
<211> LENGTH: 20
<212> TYPE: DNA

<213> ORGANISM: Artificial Sequence
<220> FEATURE:
<223> OTHER INFORMATION: Synthetic DNA

<400> SEQUENCE: 18
ctgaaggacc tcacgtcgag          20

<210> SEQ ID NO 19
<211> LENGTH: 20
<212> TYPE: DNA
<213> ORGANISM: Artificial Sequence
<220> FEATURE:
<223> OTHER INFORMATION: Synthertic DNA

<400> SEQUENCE: 19
gaacagttga ggggctacac          20

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
gtttagggtt tcttagatgc          20

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA

<400> SEQUENCE: 21
ccgtcagttt ctgcagaagt          20

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA

<400> SEQUENCE: 22
cagggtcaag ttgagcatcg          20

<210> SEQ ID NO 23
<211> LENGTH: 20
<212> TYPE: DNA
<213> ORGANISM: Artificial Sequence
<220> FEATURE:
<223> OTHER INFORMATION: Synthetic DNA

<400> SEQUENCE: 23
tgccaactca gtgaggacaa          20

<210> SEQ ID NO 24
<211> LENGTH: 20
<212> TYPE: DNA
<213> ORGANISM: Artificial Sequence
<220> FEATURE:
<223> OTHER INFORMATION: Synthetic DNA

<400> SEQUENCE: 24
tccaacaggc ctgagaaatc          20

<210> SEQ ID NO 25
<211> LENGTH: 20
<212> TYPE: DNA
<213> ORGANISM: Artificial Sequence
<220> FEATURE:
<223> OTHER INFORMATION: Synthetic DNA

<400> SEQUENCE: 25
gatgtcttcc tgggcatgtt                                         20

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
acatttgctg cccacttttc                                         20

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA

<400> SEQUENCE: 27
cgagatccct ccaaaatcaa                                         20

<210> SEQ ID NO 28
<211> LENGTH: 23
<212> TYPE: DNA
<213> ORGANISM: Artificial Sequence
<220> FEATURE:
<223> OTHER INFORMATION: Synthetic DNA

<400> SEQUENCE: 28
catgagtcct tccacgatac caa                                     23

<210> SEQ ID NO 29
<211> LENGTH: 20
<212> TYPE: DNA
<213> ORGANISM: Artificial Sequence
<220> FEATURE:
<223> OTHER INFORMATION: Synthetic DNA

<400> SEQUENCE: 29
actgcaacta tcctgacgtg                                         20

<210> SEQ ID NO 30
<211> LENGTH: 20
<212> TYPE: DNA
<213> ORGANISM: Artificial Sequence
<220> FEATURE:
<223> OTHER INFORMATION: Synthetic DNA

<400> SEQUENCE: 30
aggaaatgga ggaagctgtt                                         20

<210> SEQ ID NO 31
<211> LENGTH: 25
<212> TYPE: DNA
<213> ORGANISM: Artificial Sequence
<220> FEATURE:

```
<223> OTHER INFORMATION: Synthetic DNA

<400> SEQUENCE: 31
ccagatcttg atgtgtctct cggtc                                              25

<210> SEQ ID NO 32
<211> LENGTH: 25
<212> TYPE: DNA
<213> ORGANISM: Artificial Sequence
<220> FEATURE:
<223> OTHER INFORMATION: Synthetic DNA

<400> SEQUENCE: 32
ggatgaagtc taccaaagct cacgc                                              25
```

SMALL CHEMICAL COMPOUND WHICH PROMOTES INDUCTION OF DIFFERENTIATION OF STEM CELLS INTO INSULIN-PRODUCING CELLS AND METHOD FOR INDUCING DIFFERENTIATION OF STEM CELLS INTO INSULIN-PRODUCING CELLS USING SAID SMALL CHEMICAL COMPOUND

This application is a national stage application under 35 U.S.C. §371 of International Application No. PCT/JP2012/061549, filed May 1, 2012, entitled "LOW MOLECULAR WEIGHT COMPOUND WHICH PROMOTES INDUCTION OF DIFFERENTIATION OF STEM CELLS INTO INSULIN-PRODUCING CELLS AND METHOD FOR INDUCING DIFFERENTIATION OF STEM CELLS INTO INSULIN-PRODUCING CELLS USING SMALL CHEMICAL COMPOUND," which claims priority to Japanese Patent Application No. 2011-103281, filed May 2, 2011, the contents of both of which are hereby incorporated in their entirety by reference.

TECHNICAL FIELD

The present invention relates to a small chemical compound which promotes induction of the differentiation of stem cells into insulin-producing cells, and an agent for promoting induction of the differentiation of stem cells into insulin-producing cells, which contains the small chemical compound. Also, the present invention relates to a method for inducing the differentiation of stem cells into insulin-producing cells, using the small chemical compound, and insulin-producing cells induced by the method. Especially, the present invention relates to a compound which promotes induction of the differentiation of ES cells into insulin-producing cells, an agent for promoting induction of the differentiation of ES cells into insulin-producing cells, which contains the compound, a method for inducing the differentiation of ES cells into insulin-producing cells, using the compound, and insulin-producing cells induced by the method.

BACKGROUND ART

Pancreatic islet transplantation is a therapeutic method useful for patients with insulin-dependent diabetes mellitus. Pancreas is constituted of exocrine glands and endocrine glands. Insulin which is only one hormone having the action of lowering blood glucose among hormones in the body is secreted from pancreatic islet β cells. Pancreatic islet transplantation intends to attain regeneration by replacement of the hypoglycemic system, by isolating this pancreatic islet from pancreas and transplanting the isolated islet into a patient with insulin-dependent diabetes mellitus.

Diabetes mellitus is roughly classified into two pathological conditions. In one pathological condition, pancreatic β cells are broken and damaged by some causes to lose secretion of insulin, while in the other pathological condition, insulin is present in blood at normal level or at higher level, however, the action of insulin is lowered because of the presence of insulin resistance in peripheral tissue. The former is called type 1 diabetes mellitus or juvenile-onset diabetes mellitus, and the latter is called type 2 diabetes mellitus. Pancreatic islet transplantation is applied to type 1 diabetes mellitus.

Type 1 diabetes mellitus develops by specific breakage of pancreatic β cells producing insulin, due to autoimmune abnormality. As the fundamental therapy thereof, pancreatic islet transplantation which is one of regeneration replacement therapies for pancreatic β cells is envisaged, however, the current pancreatic islet transplantation has a major problem of deficiency in the supply amount of islet. In general, it needs several years to ten-odd years to obtain the benefit of transplantation. Therefore, transplantation is not selected as a therapeutic method suggested for a patient with type 1 diabetes mellitus in regular clinical life.

Because of the above-described reason, it has been desired to produce cells having a function corresponding to that of pancreatic islet or pancreatic β cells. Also studies of stem cells recently rapidly making advances and attracting attention report a possibility of induction of the differentiation into pancreas endocrine cells (non-patent literatures 1 to 3). For supplying cells as an alternative to human mature pancreatic islet β cells, induction of the differentiation of embryonic stem cells (ES cells), tissue stem cells or human induced pluripotent stem cells (iPS cells) into insulin-secreting cells has attracted attention, and there have ever been a lot of reports.

ES cells are pluripotent stem cells derived from an inner cell cluster of blastocyst. It has been shown that if ES cells are cultured together with embryonic mesenchymal cells, ES cells advance toward the pancreatic and hepatic lineage. The present inventors have reported that by culturing ES cells on M15 cells as the supporting cell strain, induction of the differentiation thereof into liver with high efficiency becomes possible (non-patent literature 4). The present inventors have established a technology of induction of the highly-efficient differentiation of ES cells into embryonic endodermal respiratory and digestive organs by plane culture, by a method using supporting cells (patent literatures 1 and 2). Further, by use of M15 cells, ES cells can be induced in vitro with time into meso- and endoderm, embryonic endoderm and finally region specific embryonic endoderm-derived organs. M15 feeder cells are a tool useful for generating ES cell-derived lineage-specific cell type, belonging to three kinds of germ layers (neural ectoderm, mesoderm and embryonic endoderm) (non-patent literature 6). Further, the present inventors have reported a method of induction of the efficient differentiation of ES cells into pancreas and liver, utilizing M15 cells (patent literature 3). The above-described method is, however, a method utilizing live supporting cells, thus, when a small chemical compound exerting an influence on induction of the differentiation of ES cells is screened, an influence correlated to the supporting cells cannot be excluded and a target compound cannot be screened efficiently.

CITATION LIST

Patent Literature

Patent Literature 1: WO2006/126574
Patent Literature 2: WO2008/149807
Patent Literature 3: JP2011-010653

Non Patent Literature

Non Patent Literature 1: D'Amour, K. A. et al. Production of pancreatic hormone-expressing endocrine cells from human embryonic stem cells. Nat Biotechnol 24, 1392-401 (2006).
Non Patent Literature 2: Kroon, E. et al. Pancreatic endoderm derived from human embryonic stem cells generates glucose-responsive insulin-secreting cells in vivo. Nat Biotechnol 26, 443-52 (2008).

Non Patent Literature 3: Tateishi, K. et al. Generation of insulin-secreting islet-like clusters from human skin fibroblasts. J Biol Chem 283, 31601-7 (2008).

Non Patent Literature 4: Shiraki N, Umeda K, Sakashita N, et al. Differentiation of mouse and human embryonic stem cells into hepatic lineages. Genes Cells. 2008; 13:731-746.

Non Patent Literature 5: Shiraki N, Yoshida T, Araki K, et al. Guided differentiation of embryonic stem cells into Pdx1-expressing regional-specific definitive endoderm. Stem Cells. 2008; 26:874-885.

Non Patent Literature 6: Shiraki N, Higuchi Y, Harada S, et al. Differentiation and characterization of embryonic stem cells into three germ layers. Biochem Biophys Res Commun. 2009; 381:694-699.

SUMMARY OF THE INVENTION

Problem to be Solved by the Invention

The present invention has an object of providing a substance promoting induction of the differentiation of stem cells into insulin-producing cells. The present invention has another object of providing especially a small chemical compound promoting induction of the differentiation of ES cells into insulin-producing cells. The present invention has a further object of providing a method for inducing the differentiation of ES cells into insulin-producing cells using such a compound, and an agent for promoting induction of the differentiation of insulin-producing cells. The present invention has a still further object of providing insulin-producing cells thus induced.

Means for Solving the Problem

Then, the present inventors have found that differentiation of ES cells into endodermic lineage, mesodermic lineage and ectodermic lineage can be induced by culturing ES cells using a synthetic nano fiber (sNF) matrix, without using supporting cells. Namely, it has been found that ES cells grown on a synthetic nano fiber matrix are induced into endoderm and can be induced into pancreas. Since induction efficiency in this method is sufficiently high, a candidate compound increasing the proportion of insulin-expressing cells can be obtained by using Pdx1/GFP ES cell strain or Ins1/GFP ES cell strain in high throughput screening of a small chemical compound. These contents are already filed under Japanese Patent Application No. 2010-248665. This application is incorporated herein and the entire disclosed content thereof constitutes part of the present specification. The present invention has found a small chemical compound promoting induction of the differentiation into insulin-producing cells, by use of this method, leading to completion thereof.

That is, according to the present invention, the following inventions are provided.

(1) A differentiation induction promoting agent for inducing the differentiation of mammal-derived stem cells into insulin-producing cells, comprising at least one compound selected from the group consisting of dopamine metabolism inhibitors and serotonin metabolism inhibitors.

(2) The differentiation induction promoting agent according to (1), wherein the above-described compound is at least one compound selected from the group consisting of vesicular monoamine transporter2 (VMAT2) inhibitors, dopamine or serotonin synthesis inhibitors, dopamine D2 receptor inhibitors, dopamine or serotonin agonists, monoamine oxidase inhibitors, antihistamines, H1 antagonists, histamine H2 receptor inhibitors, histamine H2 receptor agonists, selective serotonin reuptake inhibitors, dopamine antagonists and 5-HT3 receptor antagonists.

(3) The differentiation induction promoting agent according to (2), wherein the above-described compound is a vesicular monoamine transporter2 (VMAT2) inhibitor.

(4) The differentiation induction promoting agent according to (1), wherein the above-described compound is a compound selected from the group consisting of reserpine, tetrabenazine, carbidopa, α-methyltyrosine, 5HTP, bromocriptine, quinacrine dihydrochloride dihydrate, pirlindole mesylate, pargyline hydrochloride, fexofenadine HCl, hydroxyzine dihydrochloride, chlorpheniramine maleate, cimetidine, dimaprit dihydrochloride, fluvoxamine maleate, azaperone and ondansetron hydrochloride.

(5) The differentiation induction promoting agent according to (1), wherein the above-described compound is reserpine or tetrabenazine.

(6) The differentiation induction promoting agent according to any one of (1) to (5), further comprising at least one selected from the group consisting of cAMP, cAMP analogs, Gαs protein-coupled receptor agonists and Gαi protein-coupled receptor antagonists.

(7) The differentiation induction promoting agent according to (6), comprising at least one of reserpine and tetrabenazine, and at least one of cAMP and cAMP analogs.

(8) A differentiation induction promoting agent for inducing the differentiation of mammal-derived stem cells into insulin-producing cells, comprising at least one compound selected from the group consisting of acetylcholine, acetylcholine degrading enzyme inhibitors, acetylcholine receptor activators and cholinergic antagonists.

(9) The differentiation induction promoting agent according to (8), wherein the above-described compound is a compound selected from the group consisting of acetylcholine, eseroline fumarate, palmatine chloride, carbachol and ginkgolide A.

(10) A differentiation induction promoting agent for inducing the differentiation of mammal-derived stem cells into insulin-producing cells, comprising folic acid.

(11) The differentiation induction promoting agent according to any one of (1) to (10), wherein the above-described mammal-derived stem cell is an embryonic stem cell (ES cell), a tissue stem cell or an induced pluripotent stem cell (iPS cell).

(12) The differentiation induction promoting agent according to (11), wherein the above-described mammal-derived stem cell is an embryonic stem cell (ES cell).

(13) The differentiation induction promoting agent according to (11), wherein the above-described mammal-derived stem cell is a pdx1 positive cell derived from a pluripotent stem cell.

(14) A method for inducing the differentiation of mammal-derived stem cells into insulin-producing cells, comprising culturing or treating mammal-derived stem cells in a medium containing at least one compound selected from the group consisting of dopamine metabolism inhibitors and serotonin metabolism inhibitors.

(15) The differentiation inducing method according to (14), wherein the above-described compound is at least one compound selected from the group consisting of vesicular monoamine transporter2 (VMAT2) inhibitors, dopamine or serotonin synthesis inhibitors, dopamine D2 receptor inhibitors, dopamine or serotonin agonists, monoamine oxidase inhibitors, antihistamines, H1 antagonists, histamine H2 receptor inhibitors, histamine H2 receptor agonists, selective serotonin reuptake inhibitors, dopamine antagonists and 5-HT3 receptor antagonists.

(16) The differentiation inducing method according to (15), wherein the above-described compound is a vesicular monoamine transporter2 (VMAT2) inhibitor.

(17) The differentiation inducing method according to (14), wherein the above-described compound is a compound selected from the group consisting of reserpine, tetrabenazine, carbidopa, α-methyltyrosine, 5HTP, bromocriptine, quinacrine dihydrochloride dihydrate, pirlindole mesylate, pargyline hydrochloride, fexofenadine HCl, hydroxyzine dihydrochloride, chlorpheniramine maleate, cimetidine, dimaprit dihydrochloride, fluvoxamine maleate, azaperone and ondansetron hydrochloride.

(18) The differentiation inducing method according to (14), wherein the above-described compound is reserpine or tetrabenazine.

(19) The differentiation inducing method according to any one of (14) to (18), wherein the above-described medium is a medium further comprising at least one selected from the group consisting of cAMP, cAMP analogs, Gαs protein-coupled receptor agonists and Gαi protein-coupled receptor antagonists.

(20) The differentiation inducing method according to (19), wherein the above-described medium comprises at least one of reserpine and tetrabenazine, and at least one of cAMP and cAMP analogs.

(21) A method for inducing the differentiation of mammal-derived stem cells into insulin-producing cells, comprising culturing or treating mammal-derived stem cells in a medium containing at least one compound selected from the group consisting of acetylcholine, acetylcholine degrading enzyme inhibitors, acetylcholine receptor activators and cholinergic antagonists.

(22) The differentiation inducing method according to (21), wherein the above-described compound is selected from the group consisting of acetylcholine, eseroline fumarate, palmatine chloride, carbachol and ginkgolide A.

(23) A method for inducing the differentiation of mammal-derived stem cells into insulin-producing cells, comprising culturing or treating mammal-derived stem cells in a medium containing folic acid.

(24) The differentiation inducing method according to any one of (14) to (23), wherein the above-described mammal-derived stem cell is an embryonic stem cell (ES cell), a tissue stem cell or an induced pluripotent stem cell (iPS cell).

(25) The differentiation inducing method according to (24), wherein the above-described mammal-derived stem cell is an ES cell.

(26) The differentiation inducing method according to any one of (14) to (25), wherein the above-described differentiation inducing method comprises a step of culturing stem cells under at least one medium condition selected from medium conditions consisting of (1) a medium containing activin and bFGF, (2) a medium containing retinoic acid, FGF-10, B27 SUPPLEMENT and Shh signal transducing antagonist, and (3) a medium containing nicotinic acid amide.

(27) The differentiation inducing method according to (26), wherein the above-described medium condition is selected under an environment in which a synthetic nano fiber is present.

(28) Insulin-producing cells obtained by differentiation induction by the method according to any one of (14) to (27).

(29) A pharmaceutical composition comprising the differentiation induction promoting agent according to any one of (1) to (13).

Effect of the Invention

By use of the differentiation induction promoting agent and the differentiation inducing method of the present invention, the efficient differentiation of mammal-derived stem cells into insulin-producing cells can be induced. Insulin-producing cells obtained by such differentiation induction and the differentiation induction promoting agent of the present invention are not only useful for study of induction of the differentiation of stem cells into pancreatic cells, but also useful as a therapeutic medicine for type 1 diabetes mellitus.

BRIEF EXPLANATION OF DRAWINGS

FIG. 2A shows that Pdx1 is stained with Alexa 488 and insulin is stained with Alexa 568 and these are fluorescently observed, in addition to nuclear staining with DAPI, in image analysis. FIG. 2B shows that, according to image analysis using MetaXpress software, the area occupied by cells which are triply-positive for DAPI, Pdx1 and insulin is calculated, and regarded as a numerical value reflecting the number of insulin positive cells.

FIG. 9A is a view showing the expression of Drd2. FIG. 9B is a view showing increases in the differentiation of usual ES cells (NS) and dopamine D2 receptor knock-down cell cell line (KD) into insulin-producing cells, in terms of the ratio with respect to the control. Res denotes a case of addition of reserpine.

DESCRIPTION OF EMBODIMENTS

Figure 1:
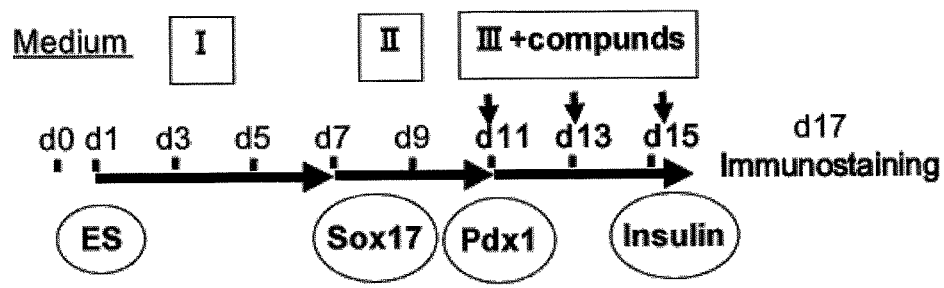
FIG. 1 is a view showing the summary of a method of screening a small chemical compound for promoting the differentiation of mouse ES cells using a nano fiber plate.

Embodiments of the present invention will be illustrated further in detail below.

The present invention relates to a compound inducing the differentiation of mammal-derived stem cells into insulin-producing cells or promoting the differentiation of these cells into insulin-producing cells, and a differentiation induction promoting agent containing the compound. Further, the present invention relates to a pharmaceutical composition for promoting insulin production, comprising the compound.

Furthermore, the present invention relates to a method for inducing the differentiation of mammal-derived stem cells into insulin-producing cells, or a method for promoting the differentiation of these cells into insulin-producing cells.

Still further, the present invention relates to insulin producing cells differentiated by the above-described method of the present invention.

The mammal-derived stem cells used in the present invention may be stem cells derived from a mammal, and its kind is not particularly restricted, and use can be made of cells derived from, for example, mouse, rat, pig, cow, monkey or human, preferably, cells derived from mouse or human.

The mammal-derived stem cells used in the present invention are mammal-derived embryonic stem cells (ES cells), tissue stem cells or induced pluripotent stem cells (iPS cells), preferably, ES cells. These stem cells can be prepared or cultured by a method known in the present technological field.

ES cells derived from a mammal can be cultured by an ordinary method, and for example, can be maintained in Glasgow minimum essential medium (Invitrogen) containing 1000 unit/ml leukemia inhibitory factor (LIF; Chemicon), 15% knockout serum replacement (KSR; Gibco), 1% fetal bovine serum (FES; Hyclone), 100 µM non-essential amino acid (NEA; Invitrogen), 2 mM L-glutamine (L-Gln; Invitrogen), 1 mM sodium pyruvate (Invitrogen), 50 unit/ml penicillin and 50 µg/ml streptomycin (PS; Invitrogen), and 100 µM β-mercaptoethanol (β-ME; Sigma), if necessary, in the presence of mitomycin C-treated mouse embryo fibroblasts (MEF) as feeder cells. The medium is not limited to this medium, and any media suitable for the object of the present invention can be used.

iPS cells are cells having pluripotency obtained by initializing somatic cells. A plurality of groups including the group of Professor Shinya Yamanaka et al. of Kyoto University, the group of Rudolf Jaenisch et al. of Massachusetts Institute of Technology, the group of James Thomson et al. of Wisconsin University, the group of Konrad Hochedlinger et al. of Harvard University, and the like succeeded in production of induced pluripotent stem cells. Induced pluripotent stem cells attract great expectations as ideal pluripotent cells showing no rejection reaction and no ethical problem. For example, International Publication WO2007/069666 describes a somatic cell nucleus initialization factor containing a gene product of Oct family genes, Klf family genes and Myc family genes, and a somatic cell nucleus initialization factor containing a gene product of Oct family genes, Klf family genes, Sox family genes and Myc family genes, and further describes a method of producing induced pluripotent stems cells by nucleus initialization of a somatic cell, comprising a step of bringing the above-described nucleus initialization factor into contact with the somatic cell.

The iPS cells used in the present invention can be produced by initializing a somatic cell. The kind of the somatic cell used here is not particularly restricted, and any somatic cells can be used. That is, the somatic cells referred to in the present invention include all cells other than genital cells among cells constituting a living organism, and may be differentiated somatic cells or undifferentiated stem cells. The derivation of the somatic cell includes mammals (for example, rodents such as mouse and the like, or primates such as human and the like), particularly preferably, mouse or human. When human somatic cells are used, somatic cells of any of fetuses, neonates or adults may be used.

The iPS cells referred to in the present invention denote stem cells having self renewal potential over a long period of time under prescribed culture condition (for example, condition for culturing ES cells) and having multipotency into ectoderm, mesoderm and endoderm under prescribed differentiation induction condition. The induced pluripotent stem cells in the present invention may also be stem cells manifesting an ability of forming teratoma when transplanted into a test animal such as mouse and the like.

For producing an iPS cell from a somatic cell, at least one initialization factor is, first, introduced into the somatic cell. In the present invention, the initialization factor means a substance (group) which can induce an iPS cell by introducing the substance into a somatic cell or by bringing the substance together with an iPS cell establishment efficiency improving factor into contact with a somatic cell, and is a proteinic factor or a gene coding this, or a small chemical compound. Specific examples of the combination of initialization factors include, but not limited to, the following combinations.

(i) Oct family, Klf family, Sox family, Myc family,
(ii) Oct family, Sox family, Nanog family, Lin28 family,
(iii) Oct family, Klf family, Sox family, Myc family, hTERT family, SV40 large T family,
(iv) Oct family, Klf family, Sox family,
(v) Oct family, Klf family, Sox family, Myc family, Glis family, or
(vi) Oct family, Klf family, Sox family, Glis family.

The family mentioned here denotes a group of proteins identified based on the primary structural homology, namely, a group of proteins having similar structures, and for example, the Oct family includes Oct1A, Oct6 and the like in addition to Oct3/4 which is a typical initialization factor for iPS cells, the Klf family includes Klf4, Klf1, Klf5 and the like, the Sox family includes Sox2, Sox1, Sox3, Sox7 and the like, the Myc family includes c-Myc, L-Myc and the like, the LIN28 family includes Lin28, Lin28B and the like, and the Glis family includes Glis1, Glis2, Glis3 and the like. In introducing initialization factors into somatic cells, introduction of various initialization factors can be carried out using a viral vector or a non-viral vector according to an introduction method described in Takahashi, K. and Yamanaka, S., Cell, 126: 663-676 (2006), Okita, K. et al., Nature, 448: 313-317 (2007), Okita, K. et al., Nature Method, 8(5): 409-412 (2011).

"Inducing the differentiation of stem cells into insulin-producing cells" referred to in the present invention has a meaning to include both a case of causing induction of the differentiation of stem cells into insulin-producing cells, and, additionally, a case of promoting induction of the differentiation thereof by combined used with other substance having an activity of inducing the differentiation of stem cells into insulin-producing cells.

In one embodiment of the present invention, the differentiation induction promoting agent of the present invention contains at least one compound selected from the group consisting of dopamine metabolism inhibitors and serotonin metabolism inhibitors.

In the present invention, the compound selected from dopamine metabolism inhibitors or serotonin metabolism inhibitors includes inhibitors of transporters of dopamine or serotonin, for example, vesicular monoamine transporter (VMAT2) inhibitors, dopamine or serotonin synthesis inhibitors, dopamine D2 receptor inhibitors, dopamine or serotonin agonists, monoamine oxidase inhibitors, MAO-A inhibitors, antihistamines, H1 antagonists, histamine H2 receptor inhibitors, histamine H2 receptor agonists, selective serotonin reuptake inhibitors, dopamine antagonists or 5-HT3 receptor antagonists. The synthesis inhibitor means a compound inhibiting synthesis, and includes, for example, inhibitors of enzymes involved in synthesis, and synthesis products inhibiting the synthesis system by the feedback action.

Examples of the dopamine metabolism inhibitor or serotonin metabolism inhibitor in the present invention include, but not limited to, reserpine or tetrabenazine as a VMAT2-inhibitor, carbidopa as a levodopadecarboxylase inhibitor, 5-hydroxytryptophan (5-HTP) as a serotonin synthesis inhibitor, α-methyltyrosine as a dopamine synthesis inhibitor, bromocriptine as a dopamine agonist, quinacrine dihydrochloride dihydrate or pargyline hydrochloride as a monoamine oxidase inhibitor, pirlindole mesylate as a MAO-A inhibitor, fexofenadine HCl as an antihistamine, hydroxyzine dihydrochloride or chlorpheniramine maleate as an H1 antagonist, cimetidine as a histamine H2 receptor inhibitor, dimaprit dihydrochloride as a histamine H2 receptor agonist, fluvoxamine maleate as a selective serotonin reuptake inhibitor, azaperone as a dopamine antagonist, ondansetron hydrochloride as a 5-HT3 receptor antagonist, and the like. Reserpine or tetrabenazine is preferable.

In another embodiment of the present invention, the differentiation induction promoting agent of the present invention can contain cAMP, cAMP analog, Gαs protein-coupled receptor agonist or Gαi protein-coupled receptor antagonist, in addition to the compound selected from the group consisting of dopamine metabolism inhibitors and serotonin metabolism inhibitors. By this, a greater effect of inducing or promoting the differentiation can be obtained. Here, the dopamine metabolism inhibitor or serotonin metabolism inhibitor has the same definition as described above.

The cAMP analog referred to in the present invention is a substance having plasma membrane permeability by changing the structure of a base part or a sugar part of cAMP, and specific examples thereof include dibutyrate-cAMP and 8-CPT-2-Me-cAMP.

Preferably, the differentiation induction promoting agent of the present invention contains at least one of reserpine and tetrabenazine, and cAMP or cAMP analog.

In another embodiment of the present invention, the differentiation induction promoting agent of the present invention contains a compound selected from the group consisting of acetylcholine, acetylcholine degrading enzyme inhibitors, acetylcholine receptor activators and cholinergic antagonists. Examples of the acetylcholine degrading enzyme inhibitor include, but not limited to, eseroline fumarate and palmatine chloride. Examples of the acetylcholine receptor activator include, but not limited to, carbachol. Examples of the cholinergic antagonist include, but not limited to, ginkgolide A.

The differentiation induction promoting agent of the present invention can also be used in combination with other substance inducing the differentiation of stem cells into insulin-producing cells. By this, induction of the differentiation into insulin-producing cells can be attained more efficiently and secretion of insulin can be caused. Examples of the other substance inducing the differentiation into insulin-producing cells include, but not limited to, nicotinamide and glucagon-like peptide-1.

The differentiation induction promoting agent of the present invention can also be used as a pharmaceutical composition, and by this, an improvement in the pancreatic function of a patient with type 1 diabetes mellitus and a patient having transplanted pancreas cells and tissue obtained by induction of the differentiation can be expected. In such a case, a pharmaceutical composition comprising the differentiation induction promoting agent of the present invention containing the above-described compound having a differentiation induction activity, and comprising an optional known pharmaceutically acceptable carrier may be prepared. The pharmaceutical composition comprising the differentiation induction promoting agent of the present invention can be administered orally or parenterally. In the case of oral administration, it can be administered in the form of capsule, tablet, granule, liquid formulation or the like. In the case of parenteral administration, it can be administered in the form of injection solution, intravenous drip formulation or the like.

When the differentiation induction promoting agent of the present invention is used as a pharmaceutical composition, the content of the compound of the present invention varies depending on the kind of the compound, the administration target, the symptom thereof and the administration method. For example, the content of reserpine is 0.01 mg to 100 mg, preferably 0.1 mg to 10 mg per day, the content of tetrabenazine, carbidopa or eseroline fumarate is 1 mg to 1000 mg, preferably 10 mg to 500 mg per day, and the content of bromocriptine is 1 mg to 1000 mg, preferably 1 mg to 100 mg per day.

In another embodiment of the present invention, the method of the present invention is a method for inducing the differentiation of stem cells into insulin-producing cells, comprising culturing or treating mammal-derived stem cells in a medium containing a compound selected from the group consisting of dopamine metabolism inhibitors and serotonin metabolism inhibitors. Here, the dopamine metabolism inhibitor or serotonin metabolism inhibitor has the same definition as described above.

The concentration of the dopamine metabolism inhibitor or serotonin metabolism inhibitor to be added into a medium is a concentration which promotes induction of the differentiation of stem cells into insulin-producing cells, and can be appropriately changed depending on the substance to be added and depending on the concentration of other substance to be added simultaneously which influences promotion of the differentiation. Though the concentration is not particularly restricted, the concentration of reserpine in a medium is 0.15 to 10.0 µM, preferably 0.15 to 2.5 µM, further preferably 0.63 µM to 1.25 µM, and the concentration of terabenazine in a medium is 0.15 to 10.0 µM, preferably 1.25 to 5.0 µM.

As the medium, known media suitable for culture or maintenance of stem cells can be used, and examples thereof include Glasgow minimum essential medium and Dulbecco's modified eagle's medium.

In the differentiation inducing method of the present invention, cAMP, cAMP analog, Gαs protein-coupled receptor agonist or Gαi protein-coupled receptor antagonist can further be contained in a medium, in addition to the compound selected from the group consisting of dopamine metabolism inhibitors or serotonin metabolism inhibitors. The concentration of cAMP or cAMP analog in a medium is 0.15 µM to 5.0 µM, preferably 0.3 µM to 0.6 µM. By this, a greater effect of inducing or promoting the differentiation can be obtained.

In another embodiment of the present invention, the differentiation induction promoting agent of the present invention contains folic acid, and the differentiation inducing method of the present invention is a method for inducing the differentiation of stem cells into insulin-producing cells, comprising culturing or treating mammal-derived stem cells in a medium containing folic acid. The concentration of folic acid in a medium is 0.08 to 10.0 µM, preferably 0.15 to 0.63 µM.

In another embodiment of the present invention, the method of the present invention is a method for inducing the differentiation of stem cells into insulin-producing cells, comprising culturing or treating mammal-derived stem cells in a medium containing a compound selected from the group consisting of acetylcholine, acetylcholine degrading enzyme inhibitors, acetylcholine receptor activators and cholinergic antagonists. The acetylcholine degrading enzyme inhibitor, acetylcholine receptor activator or cholinergic antagonist has the same definition as described above.

The concentration of acetylcholine, acetylcholine degrading enzyme inhibitor, acetylcholine receptor activator or cholinergic antagonist to be added into a medium is a concentration which promotes induction of the differentiation of stem cells into insulin-producing cells, and can be appropriately changed depending on the substance to be added and depending on the concentration of other substance to be added simultaneously which influences promotion of the differentiation. Though the concentration is not particularly restricted, for example, the concentration of palmatine chloride in a medium is 0.08 to 10.0 µM, preferably 0.15 to 0.63 µM, the concentration of eseroline fumarate in a medium is 0.15 to 10.0 µM, preferably 0.32 to 2.5 µM, and the concentration of acetylcholine in a medium is 0.15 to 5.0 µM, preferably 0.63 to 2.5 µM.

The period of adding the compound of the present invention in the method for inducing the differentiation of stem cells into insulin-producing cells of the present invention is not particularly restricted providing it is a period capable of effectively inducing the differentiation into insulin-producing cells, and a period causing appearance of Pdx1 positive cells or an earlier period is preferable.

In another embodiment of the present invention, insulin-producing cells induced from stem cells using the differentiation induction promoting agent of the present invention or the differentiation inducing method of the present invention are provided. The insulin-producing cells of the present invention are useful as a source for feeding cells instead of human mature pancreatic islet β cells in a therapeutic method of transplanting pancreatic islet into a patient with diabetic mellitus.

The present invention will be illustrated further specifically by examples below, but the present invention is not limited to the examples.

EXAMPLES

(A) Material and Method (1) ES Cell Lines

Two ES cell lines, one expressing green fluorescent protein (GFP) under the control of insulin 1 promoter, designed ING (Higuchi Y., Shiraki N., Yamane K, Qin Z., Mochitate K., Araki K., Senokuchi K., Yamagata K., Hara M., Kume K., and Kume S., Synthesized basement membranes direct the differentiation of mouse embryonic stem cells into pancreatic lineages. J. Cell Science, 123, 2733-2742, 2010), and the other one expressing GFP under the control of Pdx1 promoter, designated SK7 (Shiraki N, Yoshida T, Araki K, et al. Guided differentiation of embryonic stem cells into Pdx1-expressing regional-specific definitive endoderm. Stem Cells. 2008; 26:874-885), were used. Both cell lines were maintained on mouse embryonic fibroblast (MEF) feeders in Glasgow minimum essential medium (Invitrogen) containing 1000 units/ml leukemia inhibitory factor (LIF; Chemicon), 15% Knocked-out Serum Replacement (KSR; Gibco), 1% fetal bovine serum (FBS; Hyclone), 100 µM nonessential amino acids (NEAA; Invitrogen), 2 mM L-glutamine (L-Gln; Invitrogen), 1 mM sodium pyruvate (Invitrogen), 50 units/ml penicillin and 50 µg/ml streptomycin (PS; Invitrogen) and 100 µM β-mercaptoethanol (β-ME; Sigma), as ES maintenance medium.

(2) Synthetic Nanofiber Production by Electrospinning

The synthetic nanofiber (sNF) matrix were made by electrospinning using an adapted industrial electrospinning process with a field strength of 30 kV. The sNF matrix are composed of two kinds of polyamide polymers, A ($C_{28}O_4N_4H_{47}$)$_n$ and B ($C_{28}O_{4.4}N_4H_{47}$)$_n$, that have been cross-linked in the presence of an acid catalyst. The sNF matrixes were 200-400 nm diameter with an average of 280 nm. Pore sizes are approximately 700 nm, which is similar to the basement membrane of the cells.

(3) Differentiation of ES Cells into Pancreatic β-Cells.

For the differentiation studies, ES cells were plated at 5,000 cells per well in Corning 96 well plate with Ultra-Web Synthetic Polyamine Surface (#3873XX1, Corning Coster, Cambridge, Miss.), and cultured. The cells were cultured in Dulbecco's Modified Eagle Medium (DMEM: Invitrogen, Glasgow, UK) containing 4500 mg/L glucose, supplemented with NEAA, L-Gln, PS, β-ME, 10 μg/ml insulin (Sigma-Aldrich), 5.5 μg/ml transferrin (Sigma-Aldrich), 6.7 pg/ml selenium (Sigma-Aldrich), and 0.25% Albmax (Invitrogen), 10 ng/mL recombinant human activin-A (R&D Systems, Minneapolis, Minn.), 5 ng/mL; recombinant human bFGF for 7 days (d1-d7) (I of FIG. 1). And then, the medium was changed to RPMI 1640 medium (Invitrogen) containing 2000 mg/L glucose (Sigma, St Louis, Mo.), 1 μM Retinoic acid (Sigma-Aldrich), 50 ng/ml Human Recombinant Fibroblast Growth Factor-10 (Peprotech, Rocky Hill, N.J.), B27 SUPPLEMENT (Invitrogen) and 0.25 μM 3-Keto-N-(aminoethyl-aminocaproyl-dihydrocinnamoyl) cyclopamine Shh Signaling Antagonist II (Calbiochem, San Diego, Calif.) on d7 to d11 (II of FIG. 1). Finally, the medium was switched to DMEM containing 1000 mg/L glucose supplemented with NEAA, L-Gln, PS, β-ME, 10 μg/ml insulin (Sigma-Aldrich), 5.5 μg/ml transferrin (Sigma-Aldrich), 6.7 pg/ml selenium (Sigma-Aldrich), 0.25% Albmax (Invitrogen) and 10 mM nicotinamide (Sigma-Aldrich) on d11 to d17 (III of FIG. 1). Media were replaced every 2 days with fresh medium and growth factors until d17.

(4) Small Chemical Compounds Potentiating Differentiation of ES Cell into Insulin-Expressing Cells All tested small chemical compounds were solved in dimethyl sulfoxide (DMSO) at given concentration. Compounds were added on d11, d13 and d15 in a medium. Final concentration of DMSO was adjusted at 1.0% in all experiments for compounds.

(5) Immunocytochemistry

After 17 days cell culture, cultured ES cells were fixed in 4% paraformaldehyde in PBS for 30 min at room temperature, and rinsed several times with PBS. Then, cells were incubated in the added diluted primary antibody in 20% Blocking One (Nacalai tesque, Tokyo, Japan) in PEST (0.1% Tween-20 in PBS) in a humidified chamber for overnight at 4° C. After washing the cells in PBST, cells were incubated with the secondary antibody in 20% Blocking One for 2 hr at room temperature in dark. After washing off the secondary antibody in PBST, cells were counterstained with 6-diamidino-2-phenylindole (DAPI) (Roche Diagnostics). The following antibodies were used as First antibodies: Rabbit anti-GFP (MBL International Corp., Woburn, Mass.), Mouse anti-Insulin (Sigma). The following antibodies were used as Secondary antibodies: Alexa 568-conjugated, Alexa 488-conjugated antibodies (Invitrogen) Cells were counterstained with DAPI (Roche Diagnostics, Basel, Switzerland).

(6) Method of Screening Small Chemical Compound Promoting Differentiation of Mouse ES Cells Using Nano Fiber Plate The summary of the screening method is shown in FIG. 1. The differentiation of mouse ES cells (Pdx1/GFP) was induced for 17 days, to cause differentiation into insulin positive cells. On day 11 of culture, Pdx1-positive pancreatic precursor cells are induced and the gene expression level reaches the maximum value. On days 11, 13 and 15 of culture, a test compound dissolved in DMSO was added. A compound library/DMSO solution was added in one-100th amount into each well. By this procedure, the DMSO concentration was finally 1%. On day 17 of culture, cells were fixed with 4% PFA, then, analyzed by an immunohistologic method.

(7) Quantitative Image Analysis

Figure 2:
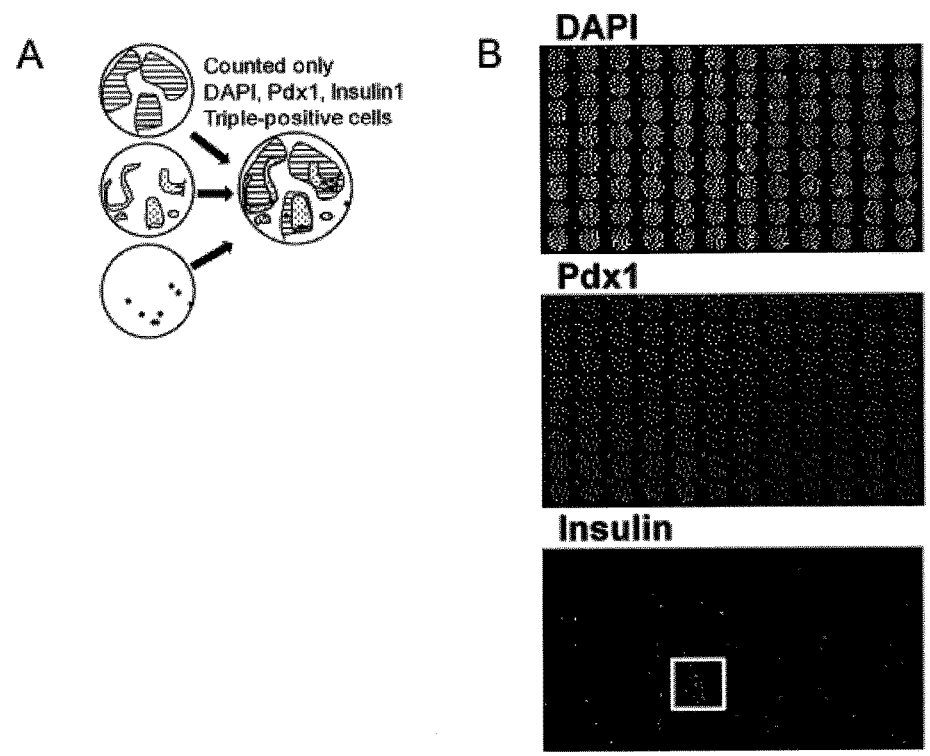
FIG. 2 is a view showing the summary of a scheme to judge as a candidate compound, in quantitative image analysis in compound screening.
Figure 3:
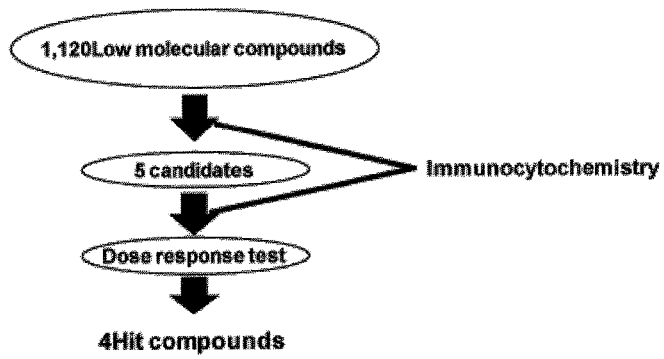
FIG. 3 is a view showing the process of screening.

Photographing of a sample image was carried out by a confocal laser scanning type high throughput confocal system (ImageXpress Ultra; manufactured by Molecular Device) (FIG. 2A). Further, the area occupied by cells which are triply-positive for DAPI, Pdx1 and insulin was calculated by image analysis using MetaXpress software, and regarded as a numerical value reflecting the number of insulin positive cells (FIG. 2B). The screening is shown in FIG. 3. The primary screening was conducted, then, the dose-responsive test was conducted. Specifically, those showing an increase in the area occupied by insulin positive cells of 1.7-fold or more than the average value of all wells were regarded as a hit compound. Those showing an increase of 1.7-fold or more among test compounds were regarded as a hit candidate compound, and further, for examining the concentration-dependent effect of these compounds, the effect was investigated again at concentrations of 0 to 10 μM.

Figure 4:
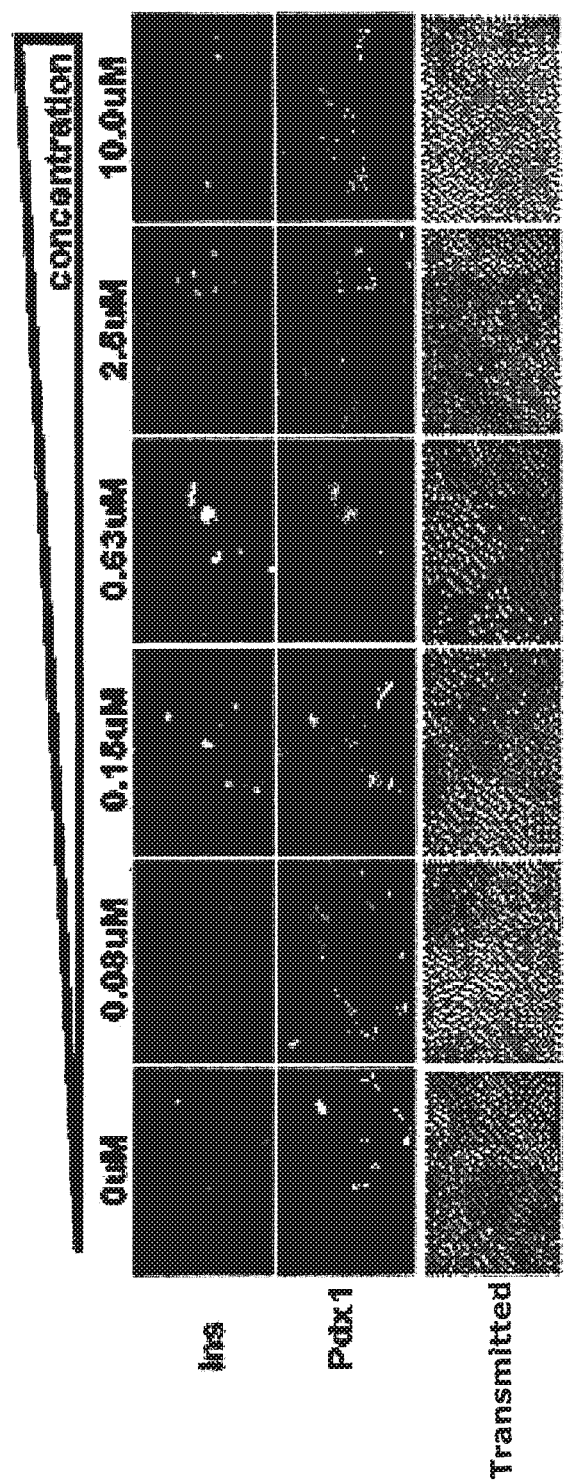
FIG. 4 is a view showing the result of examination of the concentration-dependent effect of reserpine as one embodiment of the present invention. Pdx1 is stained with Alexa 488 and insulin is stained with Alexa 568 and these are fluorescently observed. The observed results are shown in FIG. 4.

Five compounds among 1120 compounds in total showed an increase of 1.7-fold or more, thus, regarded as a hit candidate compound (FIG. 3). Further, for examining the concentration-dependent effect of these five compounds, the effect was investigated again at concentrations of 0 to 10 μM. As one example thereof, FIG. 4 shows the effect of reserpine which is a component of a differentiation induction promoting agent as one embodiment of the present invention. In this case, the maximum effect was obtained at 0.63 μM and the concentration-dependent effect was observed. In this experiment, four hit compounds were finally obtained.

(8) Gene Silencing

In the Vmat2-knockdown and Drd2-knockdown assays, Expression Arrest non-silencing control shRNA (Open Biosystems, #RHS4080), Vmat2 hRNA (Open Biosystems, #RMM3981-97058457 and #RMM3981-97058458) or Drd2 hRNA (Open Biosystems, #RMM3981-9594258) lentiviral vectors were used. For virus preparation, HEK293-FT cells (Invitrogen) were seeded on a plate medium the day before transfection. After overnight culture, the cells were transfected with lentiviral vectors and ViraPower™ Lentiviral Packaging Mix (Invitrogen) using FuGENE6 Transfection Reagent (Roche) according to the manufacturer's protocol. Cells were incubated in the ES maintenance medium for 24 hours, and viral supernatants were collected. Then, SK7 cells were infected with the viral supernatants. After incubation for 24 hours, the virus-containing medium was replaced with fresh ES maintenance medium. Further 24 hours later, the infected cells were selected using 1.5 mg/ml puromycin. The surviving cells were cloned as a knockdown-cell lines.

(9) RP-PCR Analysis

RNA extraction, reverse-transcription reactions, PCR analyses and real-time PCR analysis were carried out as previously described in Shiraki et al. (Shiraki et al., Biochem Biophys Res Commun. 2009; 381:694-699; Shiraki et al., Genes Cells. 2008; 13:731-746; Shiraki et al., Stem Cells. 2008; 26:874-885:non-patent literatures 4-6). The primer sequences for each primer set are shown in Table 1. The PCR conditions for each cycle were as flows: denaturation at 96° C. for 30 seconds, annealing at 60° C. for 2 seconds, and extension at 72° C. for 45 seconds. RT-PCR products were separated by non-denaturing polyacrylamide gel electrophoresis, stained with SYBR Green I (Molecular Probes), and visualized using a Gel Logic 200 Imaging System (Kodak). The real-time PCR conditions were as follows: denaturation at 95° C. for 3 seconds and annealing and extension at 60° C. for 30 seconds, for up to 40 cycles. Target mRNA levels, expressed as arbitrary units, were determined using a standard curve.

TABLE 1

PCR primer used for detecting gene expression

| Gene | Forward primer | Reverse primer |
| --- | --- | --- |
| Mouse | | |
| Afp | TCGTATTCCAACAGGAGG | AGGCTTTTGCTTCACCAG |
| Alb1 | CTTAAACCGATGGGCGATCTCACT | CCCCACTAGCCTCTGGCAAAAT |
| Amy | CAGGCAATCCTGCAGGAACAA | CACTTGCGGATAACTGTGCCA |
| β-actin | GTGATGGTGGGAATGGGTCA | TTTGATGTCACGCACGATTTCC |
| Krt19 | GTCCTACAGATTGACAATGC | CACGCTCTGGATCTGTGACAG |
| Gcg | ACTCACAGGGCACATTCACC | CCAGTTGATGAAGTCCCTGG |
| Ins1 | CAGCCCTTAGTGACCAGCTA | ATGCTGGTGCAGCACTGATC |
| Pdx1 | CCAAAACCGTCGCATGAAGTG | CTCTCGTGCCCTCAAGAATTTTC |
| Ppy | AGGATGGCCGTCGCATACTG | CTGAAGGACCTCACGTCGAG |
| Sox17 | GAACAGTTGAGGGGCTACAC | GTTTAGGGTTTCTTAGATGC |
| Sst | CCGTCAGTTTCTGCAGAAGT | CAGGGTCAAGTTGAGCATCG |
| Human | | |
| AFP | TGCCAACTCAGTGAGGACAA | TCCAACAGGCCTGAGAAATC |
| ALBUMIN | GATGTCTTCCTGGGCATGTT | ACATTTGCTGCCCACTTTTC |
| GAPDH | CGAGATCCCTCCAAAATCAA | CATGAGTCCTTCCACGATACCAA |
| SOX17 | ACTGCAACTATCCTGACGTG | AGGAAATGGAGGAAGCTGTT |
| PDX1 | CCAGATCTTGATGTGTCTCTCGGTC | GGATGAAGTCTACCAAAGCTCACGC |

Afp, α-fetoprotein; Alb1, albumin1; Amy, amylase; Gcg, glucagon; Ins1, insulin1; Krt19(CK19), cytokeratin 19; Ppy, pancreatic polypeptide; Sst, somatostatin

(10) Measurement of secreted insulin and cellular insulin content by enzyme-linked immunosorbent assay.

Differentiated ES cells were pre-incubated for 4 hours in low glucose (5.5 mM) Dulbecco's modified minimal essential medium with 1% fetal bovine serum. Cells were washed twice with PBS, then incubated in low—(5.5 mM) or high—(27.5 mM) glucose Dulbecco's modified minimal essential medium (with 1% fetal bovine serum) for 2 hours. Culture medium was collected, and cells were lysed with lysis buffer (0.1% Triton X-100, 1/100 (v/v) protease inhibitor cocktail in PBS). Insulin secretion into the culture medium and insulin content of the cell lysate were measured using the mouse c-peptide ELISA kit (Shibayagi. Co. Ltd., Japan).

Experiment and Result (1) High Throughput Screening of Candidate Compound Promoting Differentiation of ES Cells into Insulin-Expressing Cells The culture condition was modified so that reproducible results were obtained in a high throughput assay. The summary of the assay procedure is shown in FIG. 1. SK7 Pdx1/GFP ES cells or ING Ins1/GFP ES cells were used. On day 0 (d0), ES cells were seeded on sNF (96-well microtiter plate) and the induction activity of a small chemical compound was assayed. On day 11 (d11), individual compounds were added to each well. Compounds dissolved in DMSO (library of 1120 biologically active compounds arranged in an array) were screened. The library was diluted with DMSO at 1:100, and added into a medium according to the above-described experimental method, which was replaced by a medium containing compounds on d13 and d15. On d17, cells were stained with an anti-insulin antibody and analyzed. Compounds increasing both the number and the proportion of Ins1/GFP staining with the antibody or insulin staining were selected as the primary hit. Then, the primary hit compounds were diluted at various concentrations in the range of 0.08 to 10 μM and assayed with SK7 ES cells. The hit compounds were confirmed by dose-responsiveness. As a result, five compounds (reserpine, ellipticine, palmatine chloride, eseroline fumarate and folic acid) were identified as positive.

The concentration dependency of reserpine as one of the hit compounds was measured. The results are shown in FIG. 4.

(2) Promotion of Differentiation into Insulin-Expressing Cells Via Vmat2 Inhibition by Reserpine and Terabenazine (TBZ)

Figure 5:
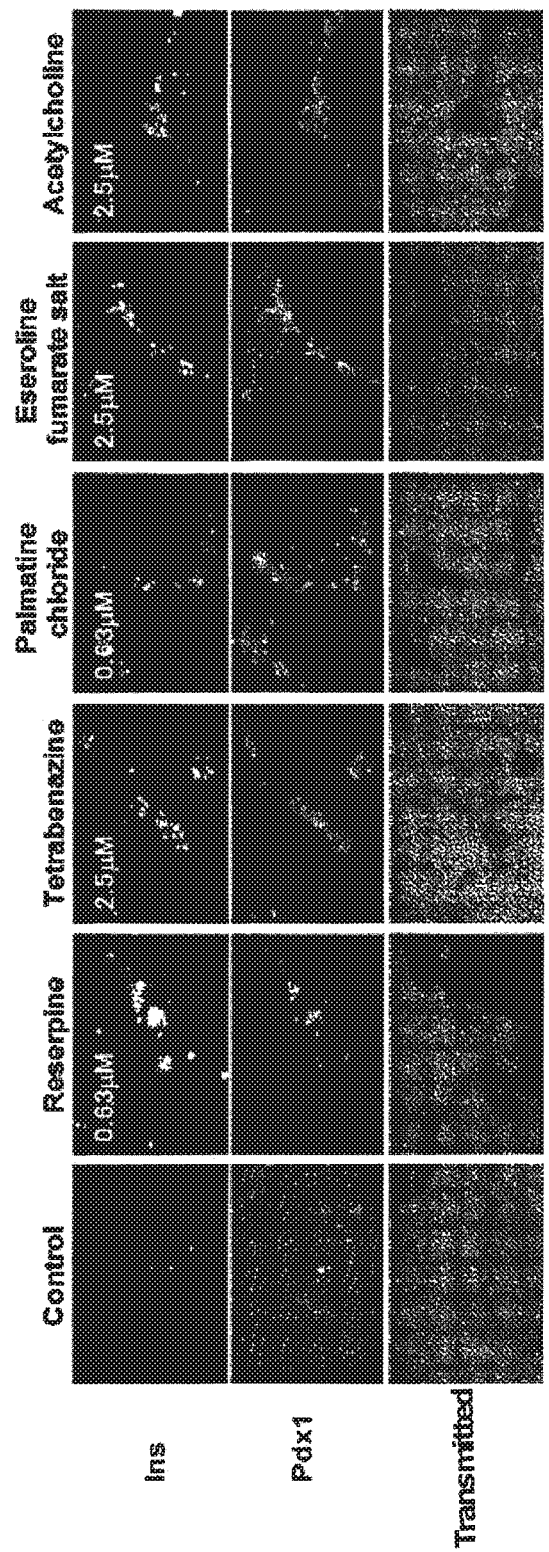
FIG. 5 is a view comparing the effects of compounds selected by compound screening on promotion of the differentiation into insulin-expressing cells. Pdx1 is stained with Alexa 488 and insulin is stained with Alexa 568 and these are fluorescently observed. The observed results are shown in FIG. 5.

Reserpine is indole alkaloid type antipsychotic and antihypertensive, and manifested strong effect and enhanced insulin-positive staining. Since the antihypertensive action by reserpine is known as a result of the action of depleting catecholamine from peripheral synapse nerve terminal by blocking vesicular monoamine transporter (VMAT2), terabenazine (TBZ) as another VMAT2-inhibitor was then investigated. As shown in FIG. 5, also addition of terabenazine showed the same effect and promoted the differentiation into insulin-expressing cells. Addition of terabenazine increased both the strength and the number of insulin-expressing cells. These results intensively suggest that VMAT2 negatively controls the differentiation of Pdx1 positive cells into insulin-producing cells.

(3) Effect of Other Compound on Promoting Differentiation into Insulin-Producing Cells Reserpine is a VMAT2 inhibitor, and also TBZ is likewise a VMAT2-inhibitor. Then, further taking note of a monoamine which is incorporated into intracellular granule by VMAT2, carbidopa, α-methyltyrosine, 5HTP and bromocriptine correlated to biosynthesis and decomposition of dopamine and serotonin were investigated, to resultantly show the same effect. Further, eseroline fumarate and palmatine chloride were examined, to observe that both the compounds increased insulin positive cells (FIG. 5). Since eseroline fumarate and palmatine chloride are an acetylcholine degrading enzyme inhibitor, acetylcholine (FIG. 5) and carbachol (not illustrated) as an acetylcholine receptor activator were tested, to observe that both the compounds increased insulin positive cells.

Figure 6:
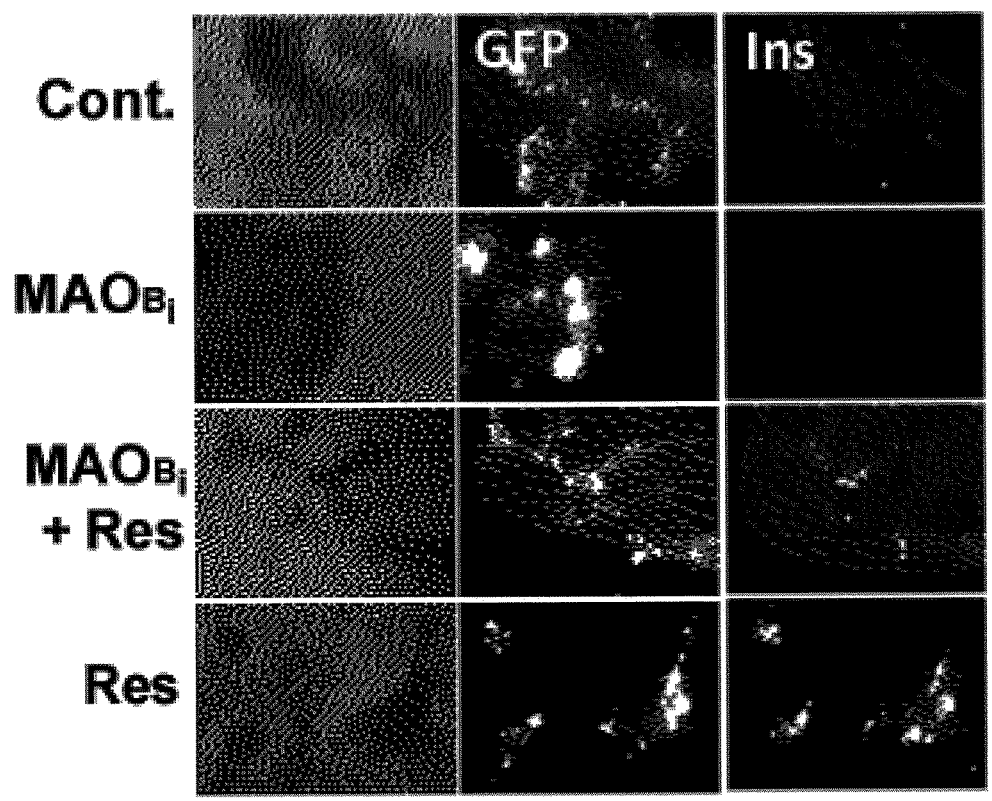
FIG. 6 is a view showing the influence of monoamine oxidase inhibitor (MAOBi) on the differentiation into insulin-expressing cells and the influence of reserpine on the differentiation promoting effect. Pdx1 is stained with Alexa 488 and insulin is stained with Alexa 568 and these are fluorescently observed. The observed results are shown in FIG. 6.
Figure 7:
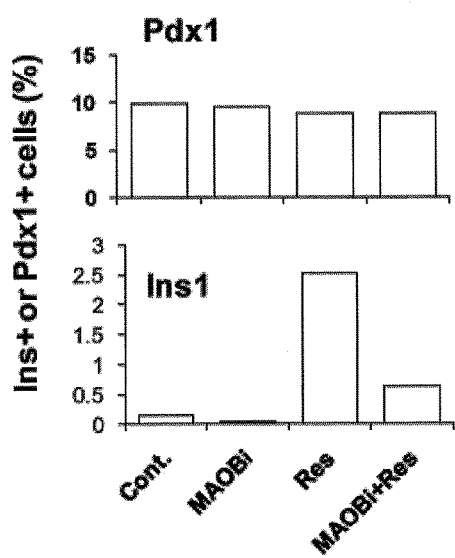
FIG. 7 is a view showing the results of FIG. 6, in terms of the ratio with respect to all cells.

The above-described results intensively suggest that incorporation of a monoamine into VMAT2-positive vesicle negatively controls the differentiation into insulin-expressing cells (suppression of differentiation). To examine suppression of the differentiation into insulin-expressing cells by a monoamine, the amount of incorporation of a monoamine into intracellular granule was tried to increase by adding a monoamine oxidase (MAO) inhibitor. MAO belongs to an enzyme family catalyzing oxidation of a monoamine, and decreases the monoamine concentration in a cell. The results are shown in FIG. 6 and FIG. 7. 1 µM Pargyline which is a MAO inhibitor (MAOBi) as a reserpine antagonist disturbs the differentiation of Pdx1 positive cells into insulin-producing cells, and its effect was deactivated by 0.63 µM reserpine. Reserpine increased insulin-producing cells, however, did not change the number of pancreatic precursor cells. Addition of a MAO inhibitor suppressed the effect of reserpine on insulin-expressing cells, without influencing the ratio of Pdx1-expressing cells. This result intensively suggests that incorporation of a monoamine into VMAT2-positive vesicle suppresses the differentiation into insulin-producing cells.

Finally, 14 compounds shown in Table 2 were identified. The numbers of insulin positive cells in respective cases are represented by relative values when the number of cells in the case of addition of no compound is represented by 1.

| Compound | Conc. (µM) | Relative value of Ins positive cells | Mechanism |
| --- | --- | --- | --- |
| Control |  | 1 |  |
| Reserpine | 0.6 | 12.2 | Blocker of dopamine uptaking into vesicle |
| Folic acid | 0.6 | 2.5 | Important for cell division and growth |
| Eseroline fumarate salt | 2.5 | 1.8 | Acetylcoline esterase inhibitor |
| Palmatine chloride | 0.6 | 1.7 | Acetylcoline esterase inhibitor |
| Tetrabenazine | 2.5 | 8.1 | VMAT-inhibitor and promotes the early metabolic degradation of monoamines |
| Acetylcholine | 2.5 | 6.9 | a neurotransmitter |
| Carbachol | 0.6 | 5 | Acetylcholine receptor activator |
| Dibutyryl- cAMP | 0.6 | 4.9 | Cell-permeable analog of cAMP that activates cAMP-dependent protein kinases (PKA). |
| Carbidopa | 0.6 | 4 | Inhibitor of dopamine and serotonin synthesis |
| 8-CPT-2-Me-cAMP | 0.3 | 3.7 | A cell-permeable cAMP analog which activates cAMP- and cGMP- dependent protein kinase. |
| alpha- Methyltyrosine | 1.3 | 3.7 | Inhibitor of dopamine synthesis |
| 5HTP | 1.3 | 3.2 | Inhibitor of serotonin synthesis |
| Bromocriptine | 0.2 | 2.1 | Dopamine agonist |

Figure 8:
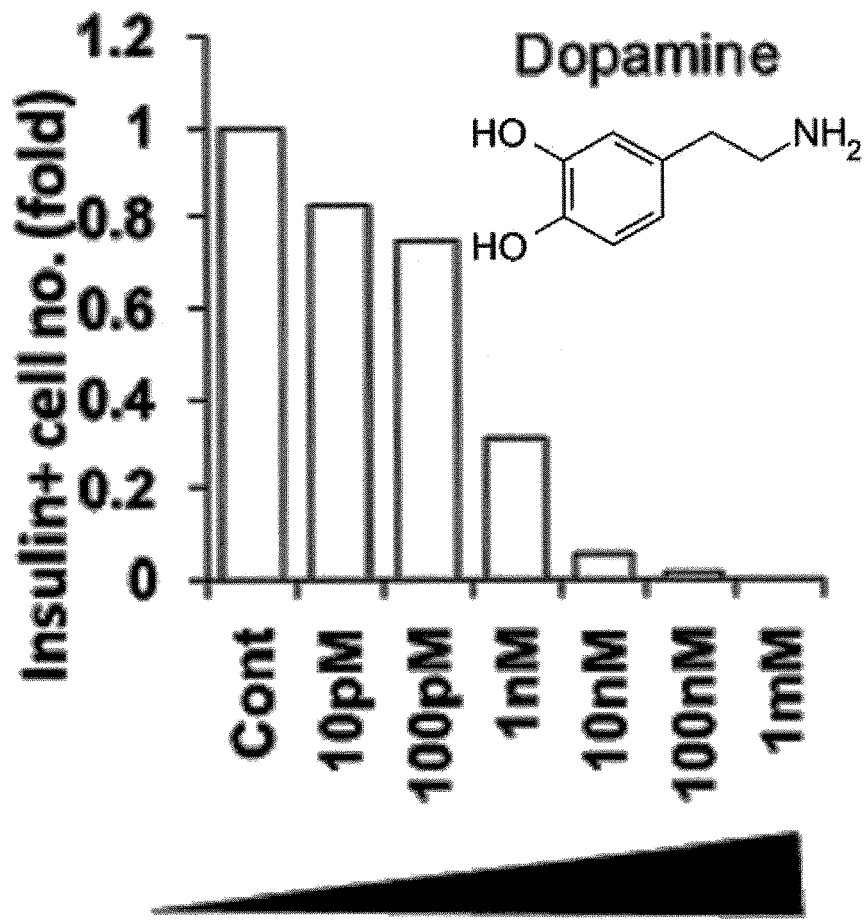
FIG. 8 is a view showing the influence of dopamine on the differentiation into insulin-producing cells.

In accordance with an idea that a monoamine inhibits the differentiation into insulin-expressing cells, α-methyltyrosine (α-MT), carbidopa, 5HTP and bromocriptine are a compound inhibiting dopamine or serotonin metabolism as shown in Table 2. α-MT is an inhibitor of tyrosine 3-monooxygenase which is an enzyme causing synthesis of catecholamine. Further, dopamine suppressed the differentiation of pancreas in a dose-dependent manner and inhibited completely the differentiation of β cells at concentrations of 100 nM or more, as shown in FIG. 8. These results show that a monoamine is a negative control factor in the differentiation into insulin-expressing cells.

Further, in similar separate experiments, it could be confirmed that also quinacrine dihydrochloride dihydrate and pargyline hydrochloride as a monoamine oxidase inhibitor, pirlindole mesylate as a MAO-A inhibitor, fexofenadine HCl as an antihistamine, hydroxyzine dihydrochloride and chlorpheniramine maleate as an H1 antagonist, cimetidine as a histamine H2 receptor inhibitor, dimaprit dihydrochloride as a histamine H2 receptor agonist, fluvoxamine maleate as a selective serotonin reuptake inhibitor, azaperone as a dopamine antagonist, ondansetron hydrochloride as a 5-HT3 receptor antagonist, and ginkgolide A as a cholinergic antagonist induce the differentiation of stem cells into insulin-producing cells.

Figure 9:
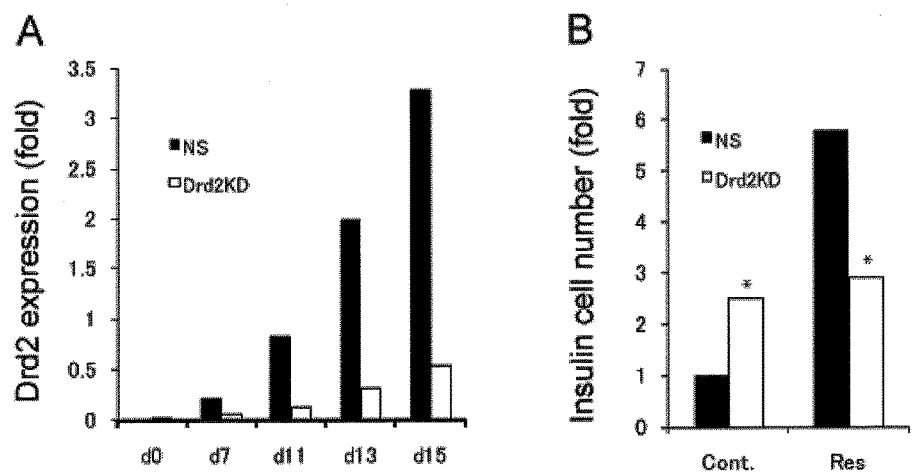
FIG. 9 is a view showing the influence of reserpine on the differentiation of dopamine D2 receptor knock-down cell cell line.

(4) Suppression of Differentiation into Insulin-Expressing Cells Via Drd2 Receptor Activation by Dopamine To confirm that a dopamine signal suppresses the differentiation into insulin-expressing cells through activation of its receptor, a dopamine D2 receptor knock-down cell line, Drd2KD was established (FIG. 9A). As shown in FIG. 9B, Drd2KD cells (inhibition of dopamine D2 receptor) increased the ability of differentiating into insulin-producing cells up to 2.5-fold. Interestingly, addition of 0.63 µM reserpine did not promote differentiation for Drd2KD cells.

The above-described results suggest that a monoamine, specifically dopamine negatively controls the differentiation into insulin-expressing cells (suppression of differentiation) via activation of its receptor.

Figure 10:
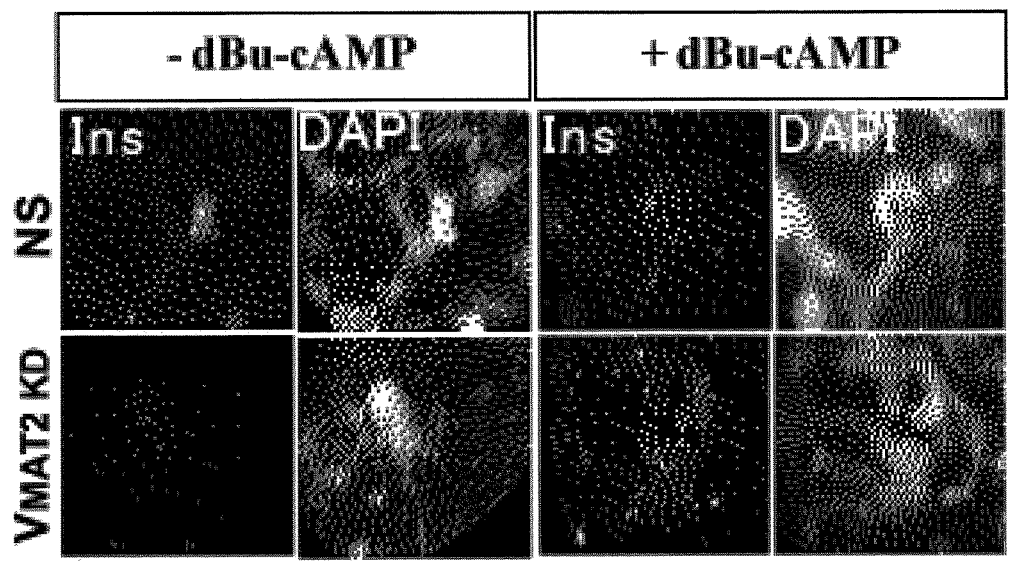
FIG. 10 is a view showing the result of examination of the influence of a cAMP analog exerted on the differentiation of usual ES cells (NS) and vesicular monoamine transporter knock-down cell line (VMAT2KD) into insulin-producing cells.
Figure 11:
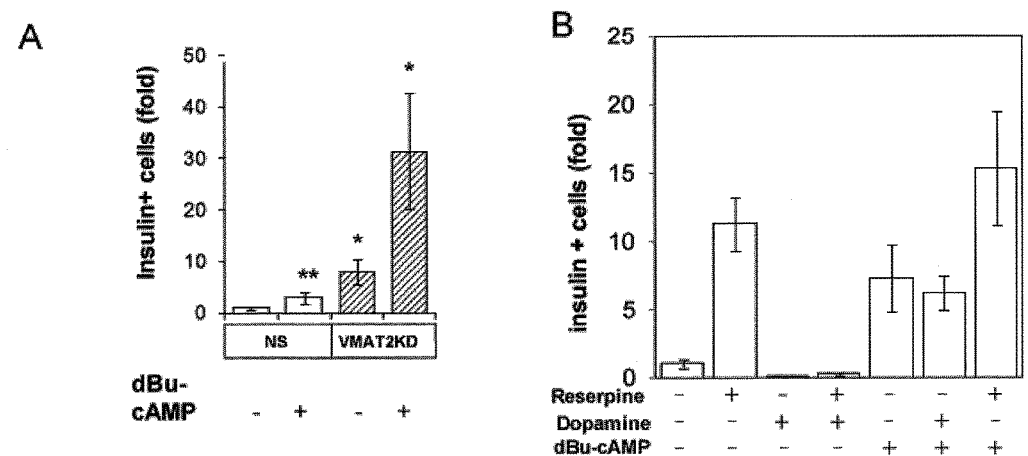
FIG. 11A is a view showing the results of FIG. 10, in terms of the ratio with respect to the control (1 in the case of normal cells with addition of no cAMP analog).
FIG. 11B is a view showing the synergistic effect of reserpine, dopamine and dBu-cAMP.

(5) Cyclic AMP as Second Messenger Positively Controlling Differentiation of Beta Cells Drd2 is known as a G protein-coupled receptor activating Gαi/o protein and having an inhibiting activity against adenyl cyclase. To identify the intracellular signal transduction phenomenon by Drd2, the effect of cAMP was examined. Addition of 0.63 µM dibutyrate-cAMP (dBu-cAMP) as a cell permeable cAMP analog to a differentiation medium on d11-d17 enhanced the differentiation into insulin-expressing cells (FIG. 10). This enhancement was stronger than that obtained when dBu-cAMP was added to VMAT2KD ES cells (FIG. 10). Quantitative analysis revealed that the number of insulin-expressing cells increased up to 2.9-fold in NS cells when dBu-cAMP was added. Only with VMAT2KD, an increase of 8-fold was observed, and further, addition of dBu-cAMP caused an increase of 31.4-fold. That is, addition of a cAMP analog generated a synergistic effect with knockdown of VMAT2. These results suggest that cAMP and VMAT2KD act synergistically in an increase in the number of insulin-producing cells (FIG. 11A).

Next, the synergistic effects of reserpine, dopamine and dBu-cAMP were confirmed. The addition concentrations thereof were 0.6 µM (reserpine), 0.1 µM (dopamine) and 0.6 µM (dBu-cAMP), respectively. Addition of dopamine decreased insulin positive cells. The increase of insulin-expressing cells mediated by reserpine was inhibited completely by addition of dopamine (FIG. 11B). It is believed that this is correlated to a fact that dopamine is the main downstream molecule of VMAT2. This result suggests that VMAT2 performs signal transduction by incorporating dopamine into intracellular granule. In contrast, also with a cAMP analog (dBu-cAMP), the number of insulin positive cells increased to about 7-fold, however, the enhancement effect of dBu-cAMP was scarcely influenced by dopamine. Further, simultaneous addition of reserpine and dBu-cAMP manifested a remarkable synergistic effect in promotion of the differentiation into insulin-expressing cells and showed increased expression of a maturation marker of β cells (FIG. 11B). These results suggest the presence of other parallel pathway stimulating cAMP production.

Figure 12:
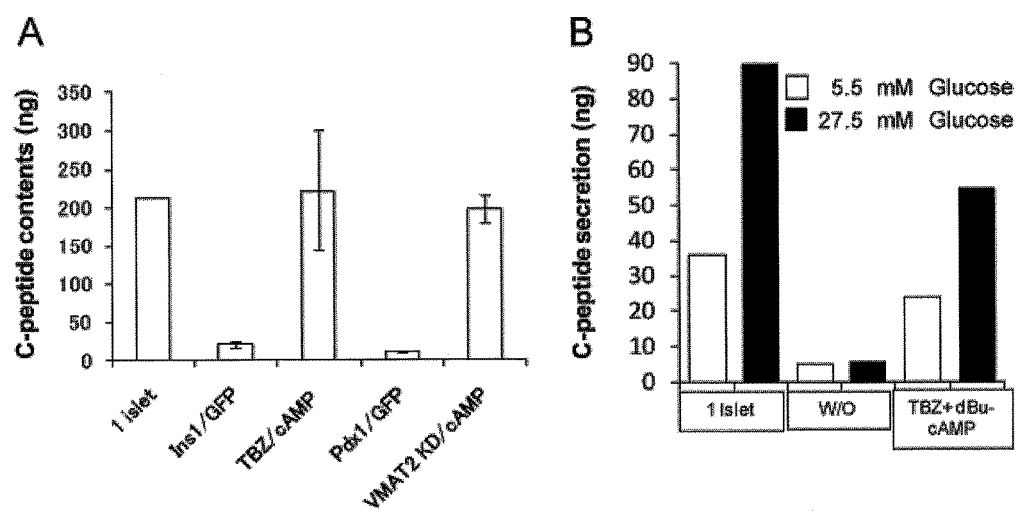
FIG. 12A is a view showing the results of examination of the amount of insulin of cells differentiated using the compound of the present invention.
FIG. 12B is a view showing the results of examination of the glucose concentration-dependent insulin secretion volume of cells differentiated using the compound of the present invention.

Next, the amount of insulin of differentiated cells was examined. ES cells differentiated by simultaneous addition of TBZ (2.5 μM) and dBu-cAMP (0.6 μM), or VMAT2KD ES cells differentiated by addition of dBu-cAMP (0.6 μM) manifested a large increase in the c-peptide amount, and its value corresponded to one pancreatic islet (FIG. 12A). Further, in an insulin secretion assay, induced insulin-expressing cells obtained in the presence of TBZ and dBu-cAMP showed glucose concentration-dependent insulin secretion (FIG. 12B). These results taught that inhibition of monoamine incorporation and activation of cAMP manifest a synergistic action.

Figure 13:
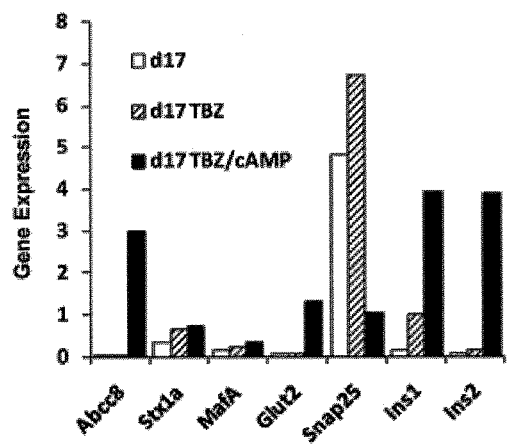
FIG. 13 is a view showing the results of examination using real time PCR of the expression of the responsive molecule to glucose sensing and secretion, in cells differentiated using the compound of the present invention.

Next, using real time PCR, expression of responsive molecules on glucose sensing and secretion was examined. The addition concentrations thereof are 2.5 μM (TBZ) and 0.6 μM (dBu-cAMP), respectively. As shown in FIG. 13, the following results were found. Expressions of Stx1 and MafA increased slightly by TBZ and dBu-cAMP. Abcc8 and Glut2 did not increase by TBZ, however, increased remarkably by dBu-cAMP. When dBu-cAMP and TBZ were added, Abcc8 and Glut2 increased to 78-fold and 15-fold, respectively, as compared with the case of addition of only TBZ. By simultaneous addition of TBZ and cAMP analog, the expression levels of Ins1 and Ins2 genes increased, while Snap25 decreased. Abcc8 and Glut2 are genes identified as a causal gene of type 2 diabetes mellitus in large scale SNP analysis, and are classified as important genes assuming a pancreas β cell function, among analogous causal genes. Further, these are important genes since they perform functions of glucose sensitivity and insulin secretion. It was shown that the expression levels of these genes were raised by the compound and the method of the present invention.

(6) Variation of Number of Pdx1/GFP Positive Cells and Number of Insulin Positive Cells by Addition of Serotonin and Histamine To confirm the influence on variations of the number of Pdx1/GFP positive cells and the number of insulin positive cells by addition of serotonin or histamine, serotonin or histamine was added at concentrations of 0, 0.08, 0.16, 0.31, 0.63, 1.25, 2.5, 5.0 and 10 μM on day 11 of culture (d11). From this day until day 17, the medium was exchanged every 2 days. On day 17, culture was stopped, and cells were stained by antibody immunostaining using an anti-GFP antibody and an anti-insulin antibody, and the number of cells was measured.

Figure 14:
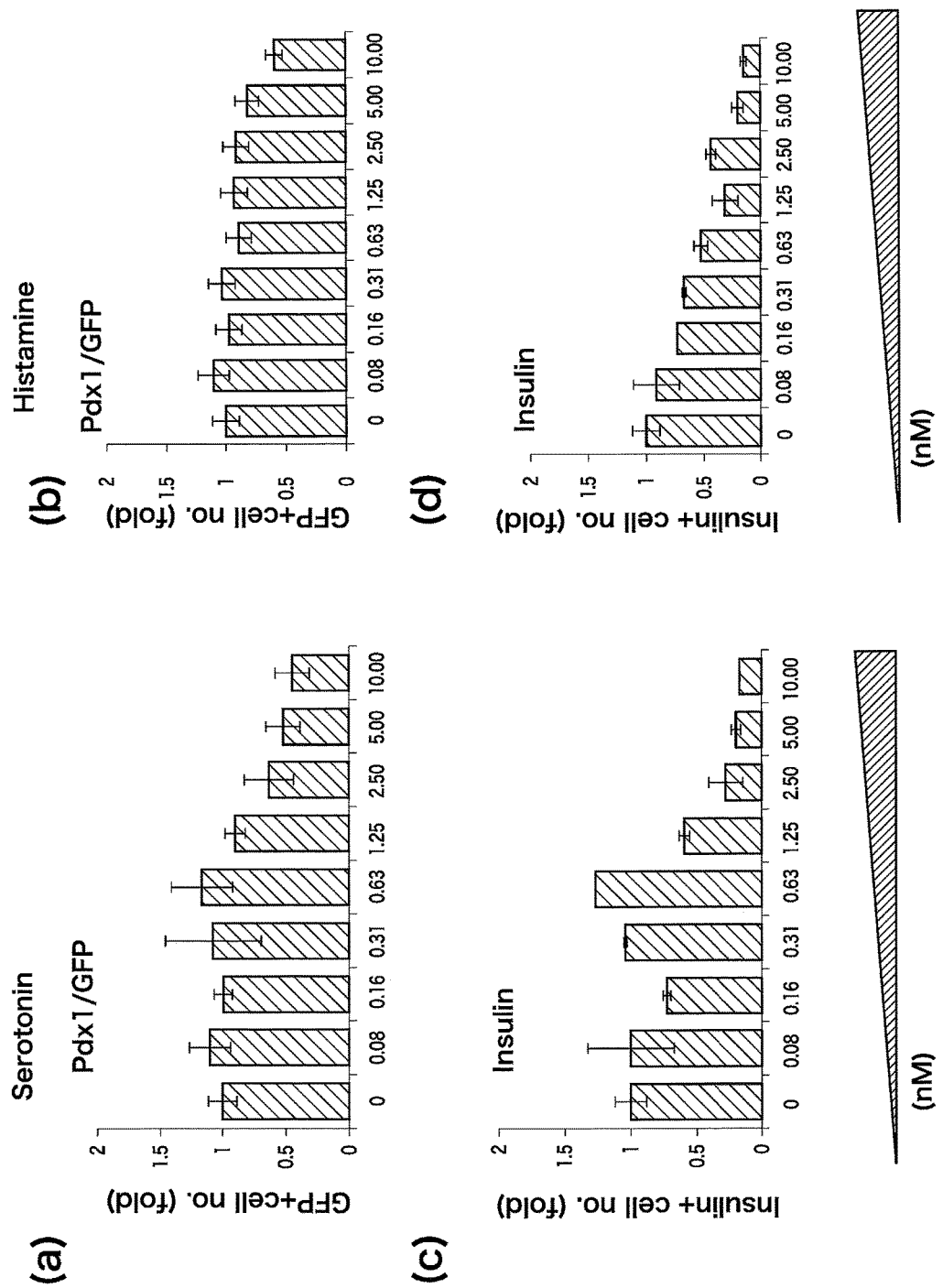
FIG. 14 is a view showing variations of the number of Pdx1/GFP positive cells and the number of insulin positive cells, by addition of serotonin and histamine.
Figure 15:
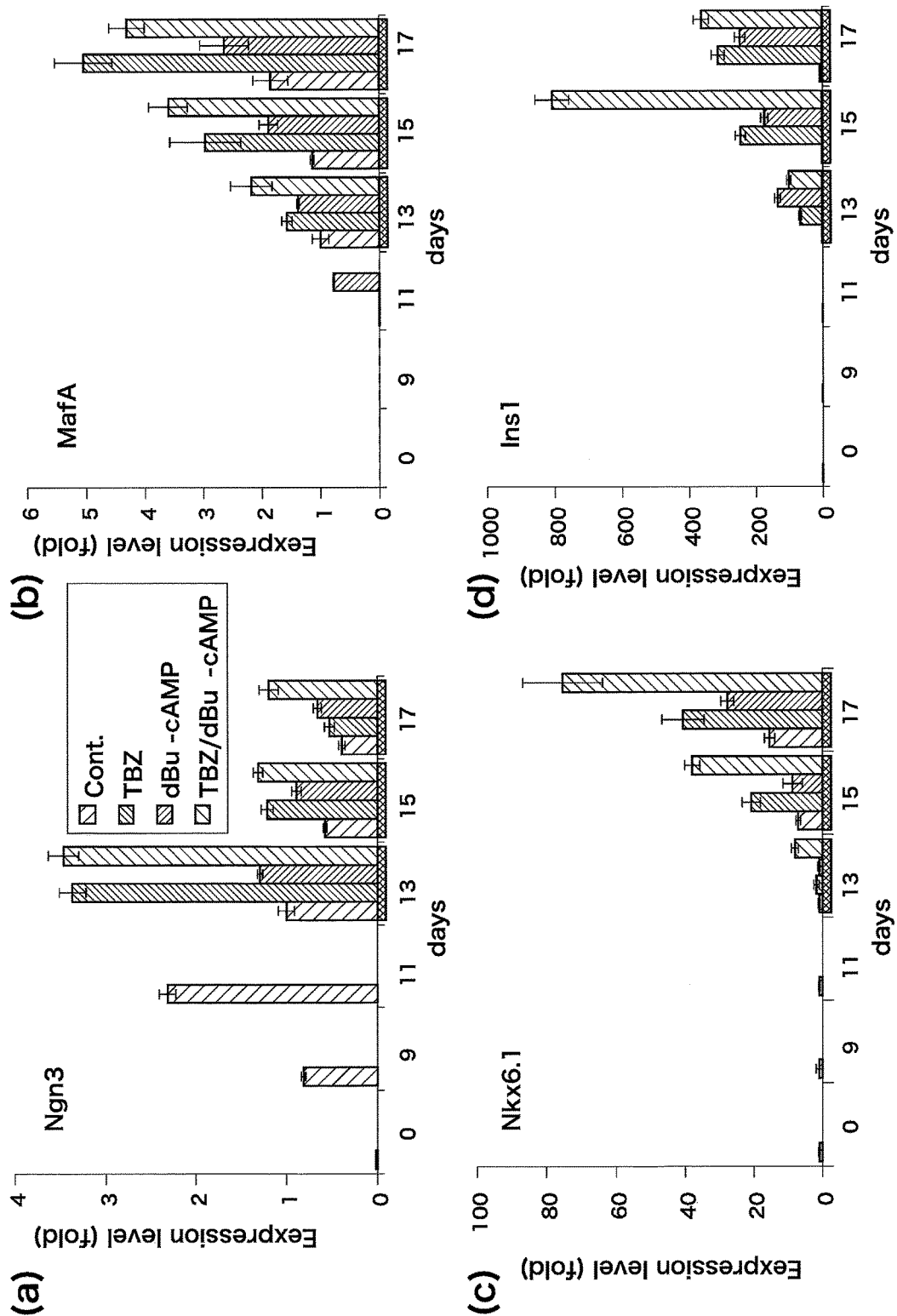
FIG. 15 is a view showing variations of the expression levels of Ngn3, Nkx6.1, MafA and Insulin1 genes when cultured with addition of four compounds.

The results are shown in FIG. 14. The number of insulin positive cells decreased in a concentration-dependent manner, by addition of serotonin or histamine. In contrast, the number of Pdx1/GFP positive cells did not vary.

(7) Variation of Expression Level of Ngn3, Nkx6.1, MafA and Insulin1 Gene

The influences of TBZ, dBu-cAMP, and TBZ and dBu-cAMP exerted on expressions of Ngn3 as a differentiation marker for pancreas endocrine cells, Nkx6.1 as a differentiation marker for pancreatic β cells, MafA specifically expressing in pancreatic Langerhans islet β cells, and Insulin1 gene were confirmed.

RNA was extracted from cells on days 0, 9 and 11 of culture. Further, RNA was collected on days 13, 15 and 17 in four cases of addition of no compound, TBZ (2.5 μM), dBu-cAMP (0.6 μM), and TBZ and dBu-cAMP (2.5 μM and 0.6 μM, respectively), every 2 days from day 11 to day 17. The expression levels of mRNA were measured by a RT-PCR method based on respective RNA samples. The expression levels are represented by ratios when the expression level on day 13 of culture in the case of addition of no compound is represented by 1.

As a result, the expression level of Ngn3 increased remarkably by TBZ on day 13 and day 15, and increased also by dBu-cAMP. The expression level of Nkx6.1 was strongly promoted by TBZ after day 15, and its effect was enhanced by dBu-cAMP. MafA was promoted by TBZ and dBu-cAMP after day 13, and the expression level increased synergistically by adding both the substances. Insulin1 was promoted by TBZ and dBu-cAMP after day 13, and an effect of synergistic increase owing to both the substances was observed after day 15.

Figure 16:
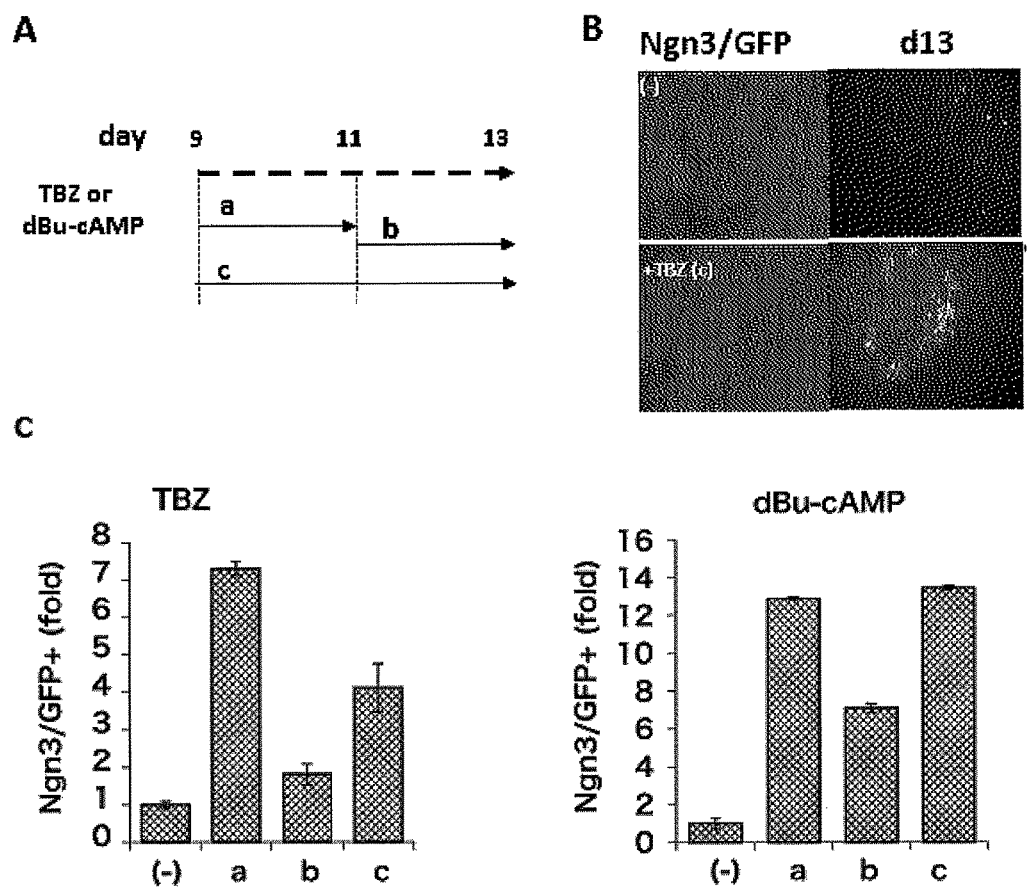
FIG. 16 is a view showing the influence of addition of TBZ or dBu-cAMP exerted on the Ngn3 positive cell inducing rate. A is a schematic view showing the addition period of TBZ or dBu-cAMP. B shows visible light photographs and fluorescence of Ngn3/GFP mouse ES cells. C is a view showing the rate of the proportions of GFP positive cells.

(8) Influence Exerted on Ngn3 Positive Cell Inducing Rate by Addition of TBZ or dBu-cAMP The influence exerted on the Ngn3 positive cell inducing rate by addition of TBZ (2.5 μM) or dBu-cAMP (0.6 μM) was confirmed. FIG. 16A is a view schematically showing the addition periods of TBZ or dBu-cAMP, and the addition periods are a) on days 9 to 11 of culture, b) on days 11 to 13 of culture, and c) on days 9 to 13 of culture.

First, the compound was not added or TBZ was added on days 9 to 13 of culture (period c), and visible light photographs and fluorescence of Ngn3/GFP mouse ES cells were observed on day 13 of culture. The results are shown in FIG. 16B. The left one is a visible light photograph and the right one is fluorescence. By addition of TBZ, an increase of Ngn3 positive cells could be confirmed.

Next, the compound was not added, or TBZ or dBu-cAMP was added under the above-described conditions a), b) and c), and the proportion of GFP positive cells on day 13 of culture was checked. The ratios of the proportions of GFP positive cells and Ngn3 positive cells when the ratio in the case of no addition is 1 are shown in FIG. 16C. As a result, the number of GFP positive cells increased in all conditions. The order of intensity of the effect was a), c), b) in descending order.

Figure 17:
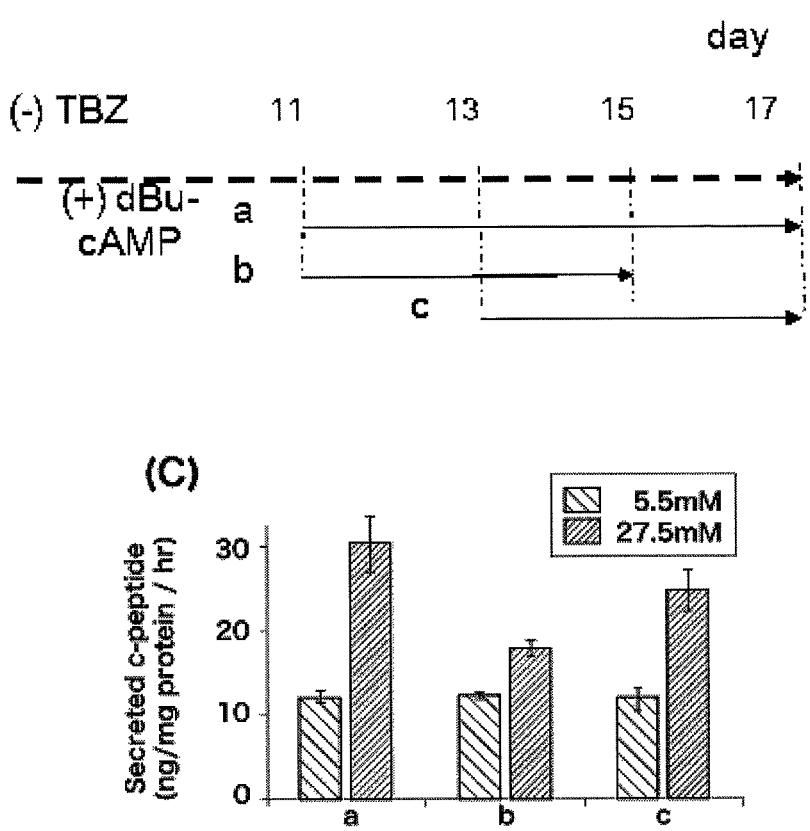
FIG. 17 is a view showing the influence of addition of dBu-cAMP on days 11 to 17 of culture exerted on glucose-responsive C-peptide secretion. The upper stage is a schematic view showing the addition period.

(9) Influence of addition of dBu-cAMP exerted on sugar-responsive C-peptide secretion dBu-cAMP (0.6 μM) was added on days 11 to 17 of culture (no addition of TBZ), and the influence exerted on sugar-responsive C-peptide secretion was confirmed. The upper stage of FIG. 17 is a view schematically showing the addition periods of dBu-cAMP, and the addition periods are a) on days 11 to 17 of culture, b) on days 11 to 15 of culture, and c) on days 13 to 17 of culture. dBu-cAMP was added under the above-described conditions a), b) and c), and the sugar-responsive C-peptide secretion volume on day 17 of culture was confirmed according to (10) of the above-described (Material and method). As a result, secretion of C-peptide increased in all conditions. The order of intensity of the effect was a), b), c) in descending order.

(10) Measurement of C-peptide content and glucose concentration-dependent insulin secretion volume when compound are added Cells were cultured in four cases of addition of no compound, TBZ (2.5 μM), dBu-cAMP (0.6 μM), and TBZ and dBu-cAMP (2.5 μM and 0.6 μM, respectively), then, GFP positive cells on day 17 were isolated by a cell sorter, and the C-peptide content and the glucose concentration-dependent insulin secretion volume were measured according to (10) of the above-described (Material and method).

Figure 18:
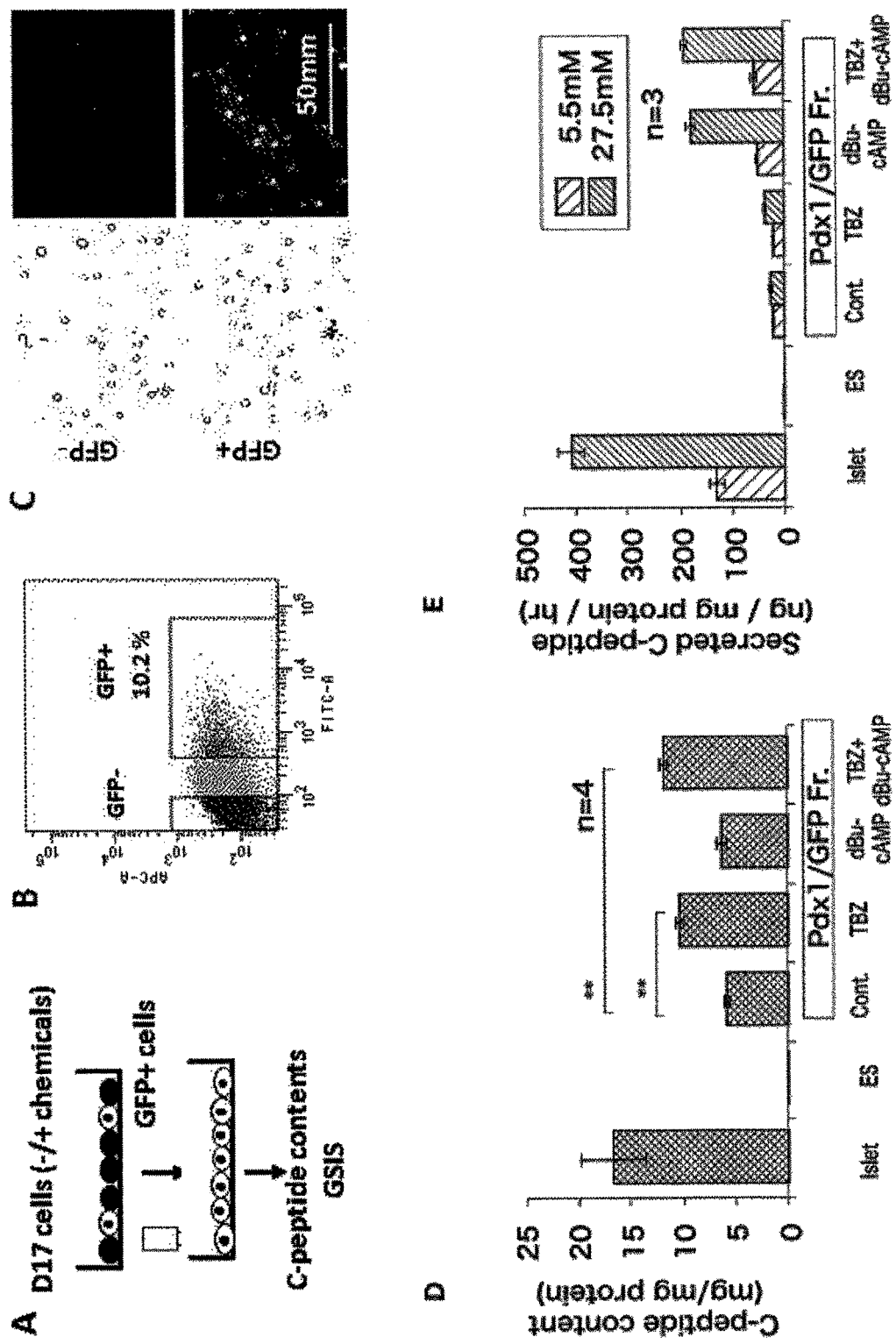
FIG. 18 is a view showing the results of measurement of the C-peptide content and the glucose concentration-dependent insulin secretion volume, after isolating GFP positive cells by a cell sorter in cases of addition of various compounds.

FIG. 18A is a view schematically showing its process. The results of measurement of distribution of the fluorescence intensity of GFP of cultured cells on day 17 of culture are shown in FIG. 18B. Visible light photographs (left) and fluorescence (right) of GFP positive cells and negative cells of the resultant cultured cells on day 17 of culture are shown in FIG. 18C. The upper stage shows GFP negative cells and the lower stage shows GFP positive cells.

Cells were cultured in four cases of addition of no compound, TBZ, dBu-cAMP, and TBZ and dBu-cAMP every 2 days from day 11 to day 17 of culture, and the C-peptide content of GFP positive cells on day 17 was measured. The results are shown in FIG. 18D. As control, the C-peptide content was measured using undifferentiated mouse ES cells and pancreatic islet extracted from a 6-week old ICR male mouse. The C-peptide content increased by addition of TBZ, and addition of TBZ and dBu-cAMP.

Using the cells cultured in four cases of addition of no compound, TBZ, dBu-cAMP, and TBZ and dBu-cAMP every 2 days from day 11 to day 17 of culture, the C-peptide secretion volume was measured when the glucose concentration was adjusted to 5.5 mM or 27.5 mM. The results are shown in FIG. 18E. As control, the C-peptide content was measured using undifferentiated mouse ES cells and pancreatic islet extracted from a 6-week old ICR male mouse. As a result, C-peptide secretion was observed by addition of dBu-cAMP when the glucose concentration was 27.5 mM.

The above-described detailed descriptions simply explain the object and the subject matter of the present invention, and do not limit the scope of the appended claims. Without deviating from the scope of the appended claims, various alterations and substitutions for embodiments described are apparent for those skilled in the art based on teachings described in the present specification.

INDUSTRIAL APPLICABILITY

The differentiation induction promoting agent and the method of the present invention are useful in the field using stem cells, for example, in the medical regeneration-related field.

The invention claimed is:

1. A method for differentiating mammal-derived stem cells into insulin-producing cells comprising culturing said stem cells in a culture medium comprising a compound which inhibits incorporation of a monoamine into a monoamine transporter 2 (VMAT2)-positive vesicle in an amount of from 0.15 µM to 40 µM to produce insulin-producing cells, wherein the compound is selected from the group consisting of tetrabenazine, and α-methyltyrosine.

2. The method according to claim 1, wherein the compound is α-methyltyrosine.

3. The method according to claim 1, wherein the compound is tetrabenazine.

4. The method according to claim 1, wherein the medium further comprises a compound which increases intracellular cAMP concentration.

5. The method according to claim 1, wherein the medium further comprises a compound selected from the group consisting of cAMP, cell permeable cAMP analogs, Gαs protein-coupled receptor agonists, and Gαi protein-coupled receptor antagonists.

6. The method according to claim 1 wherein the medium further comprises cAMP or a cell permeable cAMP analog.

7. The method according to claim 2, wherein the medium further comprises cAMP or a cell permeable cAMP analog.

8. The method according to claim 3, wherein the medium further comprises cAMP or a cell permeable cAMP analog.

9. The method according to claim 8, wherein, the medium comprises tetrabenazine in an amount of from 0.15 µM to 10.0 µM and cAMP or a cell permeable cAMP analog in an amount from 0.15 µM to 5.0 µM.

10. The method according to claim 7, wherein insulin-producing cells are glucose-responsive insulin-secreting cells.

11. The method according to claim 8, wherein insulin producing cells are glucose-responsive insulin-secreting cells.

* * * * *